US012808860B2

(12) United States Patent
Rao et al.

(10) Patent No.: US 12,808,860 B2
(45) Date of Patent: Nov. 24, 2026

(54) METHODS AND AGENTS FOR ASSESSING T-CELL FUNCTION AND PREDICTING RESPONSE TO THERAPY

(71) Applicant: EPIAXIS THERAPEUTICS PTY LTD, Herston (AU)

(72) Inventors: Sudha Rao, Red Hill (AU); Robert Mccuaig, Stafford Heights (AU)

(73) Assignee: Epiaxis Therapeutics PTY LTD, Herston (AU)

( * ) Notice: Subject to any disclaimer, the term of this patent is extended or adjusted under 35 U.S.C. 154(b) by 1284 days.

(21) Appl. No.: 17/433,737

(22) PCT Filed: Feb. 27, 2020

(86) PCT No.: PCT/AU2020/050172

§ 371 (c)(1),
(2) Date: Aug. 25, 2021

(87) PCT Pub. No.: WO2020/172712

PCT Pub. Date: Sep. 3, 2020

(65) Prior Publication Data

US 2022/0146495 A1 May 12, 2022

(30) Foreign Application Priority Data

Feb. 27, 2019 (AU) ................................ 2019900628

(51) Int. Cl.
*G01N 33/50* (2006.01)
*G01N 33/536* (2006.01)
*G01N 33/575* (2026.01)

(52) U.S. Cl.
CPC ....... *G01N 33/505* (2013.01); *G01N 33/5091* (2013.01); *G01N 33/536* (2013.01); *G01N 33/5758* (2026.01); *G01N 2333/4703* (2013.01); *G01N 2440/10* (2013.01); *G01N 2440/12* (2013.01)

(58) Field of Classification Search
CPC ....................... G01N 2800/52; G01N 2440/12
See application file for complete search history.

(56) References Cited

FOREIGN PATENT DOCUMENTS

JP 2016-534363 11/2016
WO WO 2015/036781 3/2015
WO WO 2016/061456 4/2016
WO WO 2016/161282 10/2016
WO WO 2018/104909 6/2018

OTHER PUBLICATIONS

Rodriguez et. al. (Development. 139:3870-3879 (2012) (Year: 2012).*
Wen et. al. Bioinformatics. 32(20):3107-3115. (2016) (Year: 2016).*
Li et. al. Frontiers in Immunology. 9(2961):1-13. (2018) (Year: 2018).*
Buuh et. al. Nucleic Acids Research. 40: D261-D270. (2012) (Year: 2012).*
Wayback Machine of PhosphoSitePlus: Browse MS2 Data by Cell line. Oct. 13, 2016 (Year: 2016).*
Grimes et. al. Sci. Signal. 11(531): 1-16. (2018) (Year: 2018).*
Kamphorst et. al. Immunology and Inflammation. 114(19):4993-4998 (2017) (Year: 2017).*
Buggert et al., "T-bet and Eomes are Differentially Linked to the Exhausted Phenotype of CD8+ T Cells in HIV Infection," PLOS Pathogens, 10(7): 15 pgs. (Jul. 2014).
Intlekofer et al., "Effector and memory CD8+ T cell fate coupled by T-bet and eomesodermin," Nature Immunology, 6(12): 1236-1244, (Dec. 2005.
McLane et al., "Differential Localization of T-bet and Eomes in CD8 T Cell Memory Polulations," J. Immunol., 190:3207-3215 (Mar. 1, 2013).
Search Report & Written Opinion issued in Appl. No. PCT/AU2020/050172 (2020).
Kim et al., Post-Translational Modifications in Transcription Factors that Determine T Helper Cell Differentiation. Mol Cells. May 31, 2021;44(5):318-327.
Zhang et al., T-bet and Eomes govern differentiation and function of mouse and human NK cells and ILC1. Eur J Immunol. May 2018;48(5):738-750.

* cited by examiner

*Primary Examiner* — Julie Wu
*Assistant Examiner* — Francesca Edgingtongiordano
(74) *Attorney, Agent, or Firm* — Casimir Jones, S.C.; Mary Ann D. Brow

(57) ABSTRACT

This disclosure relates generally to methods and agents for assessing T-cell function and for predicting responses to therapy. More particularly, the present invention relates to methods and agents for detecting different forms of Eomesodermin (EOMES) in T-cells, which are useful for assessing the function of a T-cell, for assessing the immune function of a subject, for predicting the likelihood of response of a cancer patient to therapy including immunotherapy, for stratifying a cancer patient as a likely responder or non-responder to a therapy, and for managing treatment of a cancer patient.

14 Claims, 7 Drawing Sheets

Specification includes a Sequence Listing.

A.

B.

C.

[SEQ ID NO: 6]

| EOMES | Residues | NLS Binding Determinants | | | | | Residues |
|---|---|---|---|---|---|---|---|
| | | P1 | P2 | P3 | P4 | P5 | |
| EOMES | 640 | C | K | R | R | R | 644 |

[SEQ ID NO: 7]

D.

[SEQ ID NO: 6]

[SEQ ID NO: 8]

[SEQ ID NO: 9]

E.

F.

A.

B.

C.

A.

B.

SEQUENCE LISTING

```
<160> NUMBER OF SEQ ID NOS: 11

<210> SEQ ID NO 1
<211> LENGTH: 686
<212> TYPE: PRT
<213> ORGANISM: Homo sapiens

<400> SEQUENCE: 1

Met Gln Leu Gly Glu Gln Leu Leu Val Ser Ser Val Asn Leu Pro Gly
1               5                   10                  15

Ala His Phe Tyr Pro Leu Glu Ser Ala Arg Gly Gly Ser Gly Gly Ser
            20                  25                  30

Ala Gly His Leu Pro Ser Ala Ala Pro Ser Pro Gln Lys Leu Asp Leu
        35                  40                  45

Asp Lys Ala Ser Lys Lys Phe Ser Gly Ser Leu Ser Cys Glu Ala Val
    50                  55                  60
```

```
Ser Gly Glu Pro Ala Ala Ala Ser Ala Gly Ala Pro Ala Ala Met Leu
65                  70                  75                  80

Ser Asp Thr Asp Ala Gly Asp Ala Phe Ala Ser Ala Ala Ala Val Ala
                85                  90                  95

Lys Pro Gly Pro Pro Asp Gly Arg Lys Gly Ser Pro Cys Gly Glu Glu
            100                 105                 110

Glu Leu Pro Ser Ala Ala Ala Ala Ala Ala Ala Ala Ala Ala Ala Ala
        115                 120                 125

Ala Ala Thr Ala Arg Tyr Ser Met Asp Ser Leu Ser Ser Glu Arg Tyr
    130                 135                 140

Tyr Leu Gln Ser Pro Gly Pro Gln Gly Ser Glu Leu Ala Ala Pro Cys
145                 150                 155                 160

Ser Leu Phe Pro Tyr Gln Ala Ala Ala Gly Ala Pro His Gly Pro Val
                165                 170                 175

Tyr Pro Ala Pro Asn Gly Ala Arg Tyr Pro Tyr Gly Ser Met Leu Pro
            180                 185                 190

Pro Gly Gly Phe Pro Ala Ala Val Cys Pro Pro Gly Arg Ala Gln Phe
        195                 200                 205

Gly Pro Gly Ala Gly Ala Gly Ser Gly Ala Gly Gly Ser Ser Gly Gly
    210                 215                 220

Gly Gly Gly Pro Gly Thr Tyr Gln Tyr Ser Gln Gly Ala Pro Leu Tyr
225                 230                 235                 240

Gly Pro Tyr Pro Gly Ala Ala Ala Ala Gly Ser Cys Gly Gly Leu Gly
                245                 250                 255

Gly Leu Gly Val Pro Gly Ser Gly Phe Arg Ala His Val Tyr Leu Cys
            260                 265                 270

Asn Arg Pro Leu Trp Leu Lys Phe His Arg His Gln Thr Glu Met Ile
        275                 280                 285

Ile Thr Lys Gln Gly Arg Arg Met Phe Pro Phe Leu Ser Phe Asn Ile
    290                 295                 300

Asn Gly Leu Asn Pro Thr Ala His Tyr Asn Val Phe Val Glu Val Val
305                 310                 315                 320

Leu Ala Asp Pro Asn His Trp Arg Phe Gln Gly Gly Lys Trp Val Thr
                325                 330                 335

Cys Gly Lys Ala Asp Asn Asn Met Gln Gly Asn Lys Met Tyr Val His
            340                 345                 350

Pro Glu Ser Pro Asn Thr Gly Ser His Trp Met Arg Gln Glu Ile Ser
        355                 360                 365

Phe Gly Lys Leu Lys Leu Thr Asn Asn Lys Gly Ala Asn Asn Asn Asn
    370                 375                 380

Thr Gln Met Ile Val Leu Gln Ser Leu His Lys Tyr Gln Pro Arg Leu
385                 390                 395                 400

His Ile Val Glu Val Thr Glu Asp Gly Val Glu Asp Leu Asn Glu Pro
                405                 410                 415

Ser Lys Thr Gln Thr Phe Thr Phe Ser Glu Thr Gln Phe Ile Ala Val
            420                 425                 430

Thr Ala Tyr Gln Asn Thr Asp Ile Thr Gln Leu Lys Ile Asp His Asn
        435                 440                 445

Pro Phe Ala Lys Gly Phe Arg Asp Asn Tyr Asp Ser Ser His Gln Ile
    450                 455                 460

Val Pro Gly Gly Arg Tyr Gly Val Gln Ser Phe Phe Pro Glu Pro Phe
465                 470                 475                 480

Val Asn Thr Leu Pro Gln Ala Arg Tyr Tyr Asn Gly Glu Arg Thr Val
```

```
                485                 490                 495

Pro Gln Thr Asn Gly Leu Leu Ser Pro Gln Gln Ser Glu Glu Val Ala
            500                 505                 510

Asn Pro Pro Gln Arg Trp Leu Val Thr Pro Val Gln Gln Pro Gly Thr
        515                 520                 525

Asn Lys Leu Asp Ile Ser Ser Tyr Glu Ser Glu Tyr Thr Ser Ser Thr
    530                 535                 540

Leu Leu Pro Tyr Gly Ile Lys Ser Leu Pro Leu Gln Thr Ser His Ala
545                 550                 555                 560

Leu Gly Tyr Tyr Pro Asp Pro Thr Phe Pro Ala Met Ala Gly Trp Gly
                565                 570                 575

Gly Arg Gly Ser Tyr Gln Arg Lys Met Ala Ala Gly Leu Pro Trp Thr
            580                 585                 590

Ser Arg Thr Ser Pro Thr Val Phe Ser Glu Asp Gln Leu Ser Lys Glu
        595                 600                 605

Lys Val Lys Glu Glu Ile Gly Ser Ser Trp Ile Glu Thr Pro Pro Ser
    610                 615                 620

Ile Lys Ser Leu Asp Ser Asn Asp Ser Gly Val Tyr Thr Ser Ala Cys
625                 630                 635                 640

Lys Arg Arg Arg Leu Ser Pro Ser Asn Ser Ser Asn Glu Asn Ser Pro
                645                 650                 655

Ser Ile Lys Cys Glu Asp Ile Asn Ala Glu Glu Tyr Ser Lys Asp Thr
            660                 665                 670

Ser Lys Gly Met Gly Gly Tyr Tyr Ala Phe Tyr Thr Thr Pro
        675                 680                 685


<210> SEQ ID NO 2
<211> LENGTH: 12
<212> TYPE: PRT
<213> ORGANISM: Homo sapiens

<400> SEQUENCE: 2

Val Thr Tyr Ser Cys Lys Arg Arg Arg Leu Ser Pro
1               5                   10


<210> SEQ ID NO 3
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: ACETYLATION

<400> SEQUENCE: 3

Val Thr Tyr Ser Cys Lys Arg Arg Arg Leu Ser Pro
1               5                   10


<210> SEQ ID NO 4
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: METHYLATION

<400> SEQUENCE: 4

Val Thr Tyr Ser Cys Lys Arg Arg Arg Leu Ser Pro
1               5                   10
```

<210> SEQ ID NO 5
<211> LENGTH: 19
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa=selenocysteine
<220> FEATURE:
<221> NAME/KEY: MOD_RES
<222> LOCATION: (10)..(10)
<223> OTHER INFORMATION: METHYLATION

<400> SEQUENCE: 5

Arg Gln Xaa Ile Ser Phe Gly Lys Leu Lys Leu Thr Asn Asn Lys Gly
1 5 10 15

Ala Asn Asn

<210> SEQ ID NO 6
<211> LENGTH: 13
<212> TYPE: PRT
<213> ORGANISM: Homo sapiens

<400> SEQUENCE: 6

Val Tyr Thr Ser Ala Cys Lys Arg Arg Arg Leu Ser Pro
1 5 10

<210> SEQ ID NO 7
<211> LENGTH: 5
<212> TYPE: PRT
<213> ORGANISM: Homo sapiens

<400> SEQUENCE: 7

Cys Lys Arg Arg Arg
1 5

<210> SEQ ID NO 8
<211> LENGTH: 13
<212> TYPE: PRT
<213> ORGANISM: Artificial sequence
<220> FEATURE:
<223> OTHER INFORMATION: Synthetic construct

<400> SEQUENCE: 8

Val Tyr Thr Ser Ala Cys Arg Arg Arg Arg Leu Ser Pro
1 5 10

<210> SEQ ID NO 9
<211> LENGTH: 13
<212> TYPE: PRT
<213> ORGANISM: Artificial sequence
<220> FEATURE:
<223> OTHER INFORMATION: Synthetic construct

<400> SEQUENCE: 9

Val Tyr Thr Ser Ala Cys Phe Arg Arg Arg Leu Ser Pro
1 5 10

<210> SEQ ID NO 10
<211> LENGTH: 19
<212> TYPE: PRT
<213> ORGANISM: Homo sapiens

<400> SEQUENCE: 10

Arg Gln Glu Ile Ser Phe Gly Lys Leu Lys Leu Thr Asn Asn Lys Gly
1 5 10 15

-continued

```
Ala Asn Asn

<210> SEQ ID NO 11
<211> LENGTH: 7
<212> TYPE: PRT
<213> ORGANISM: Homo sapiens

<400> SEQUENCE: 11

Lys Leu Lys Thr Asn Asn Lys
1               5
```

METHODS AND AGENTS FOR ASSESSING T-CELL FUNCTION AND PREDICTING RESPONSE TO THERAPY

CROSS REFERENCE TO RELATED APPLICATIONS

This application is a U.S. nationalization under 35 U.S.C. § 371 of International Application No. PCT/AU2020/050172, filed 27 Feb. 2020, which claims priority to Australian Patent Application No. 2019900628, filed 27 Feb. 2019. The disclosures set forth in the referenced applications are incorporated herein by reference in their entireties.

SEQUENCE LISTING

The text of the computer readable sequence listing filed herewith, titled "41276-251_SEQUENCE_LISTING", created Aug. 26, 2026, having a file size of 12,408 bytes, is hereby incorporated by reference in its entirety.

FIELD OF THE INVENTION

This disclosure relates generally to methods and agents for assessing T-cell function and for predicting responses to therapy. More particularly, the present invention relates to methods and agents for detecting different forms of Eomesodermin (EOMES) in T-cells, which are useful for assessing the function of a T-cell, for assessing the immune function of a subject, for predicting the likelihood of response of a cancer patient to therapy including immunotherapy, for stratifying a cancer patient as a likely responder or non-responder to a therapy, and for managing treatment of a cancer patient.

RELATED APPLICATIONS

This application claims priority to Australian Provisional Application No. 2019900628 entitled "Method and agents for assessing T-cell function and predicting response to therapy" filed 27 Feb. 2019, the content of which is incorporated herein by reference in its entirety.

BACKGROUND OF THE INVENTION

Cancer is a significant cause of morbidity and mortality worldwide. While the standards of care for many different cancer types have greatly improved over the years, current standards of care still fail to meet the need for effective therapies to improve treatment of cancer. The clinical use of immuno-oncology agents targeting cytotoxic T-lymphocyte-associated protein 4 (CTLA-4) and the programmed cell death receptor-1 (PD-1) and its ligand PD-L1, have resulted in improvements in the standard of care for treating many cancer types. While these checkpoint inhibitors have produced improved clinical responses in certain cancers, durable clinical responses only occur in approximately 10-45% of patients. Moreover, a significant number of tumors are either resistant or become refractory. For example, about 20-50% of melanoma and lung cancers will respond significantly to immunotherapies, while others will not. Thus, identifying which subjects are better candidates for cancer therapy is highly advantageous from a health care and patient quality of life perspective.

Accordingly, there remains a need in the art for methods and agents that aid in predicting response to therapy including immunotherapy, with improved accuracy.

SUMMARY OF THE INVENTION

The present invention arises in part from the determination that different post-translational modifications of EOMES in a T-cell were associated with localization of this transcription factor to different cellular compartments. Moreover, the different post-translational modifications were associated with different T-cell function and responsiveness to the cancer therapy. In particular, the present inventors have found that different post-translational modifications of a lysine (i.e., EOMES-641K) in the nuclear localization sequence (NLS) of EOMES were associated with localization of EOMES to the nucleus or to the cytoplasm. More specifically, it was found that acetylation of EOMES-641K (i.e., EOMES-263K-Ac) was associated with biased localization of EOMES to the nucleus. Of interest, it was found that this acetylated form of EOMES was also associated with T-cell exhaustion and resistance or non-responsiveness to therapy. Conversely, it was found that methylation of EOMES-641K (i.e., EOMES-641K-Me) was generally associated with more biased localization of EOMES to the cytoplasm of the T-cell. This form of EOMES was also associated with a T-cell with competent immune function, and correlated with responsiveness to cancer therapy. The present inventors have also shown that post-translational modification of a lysine in the DNA binding domain of EOMES (i.e. EOMES-373K) correlated with responsiveness to cancer therapy. Specifically, methylation of EOMES-373K (i.e. EOMES-373K-Me) was associated with biased cytoplasmic localization and responsiveness to cancer therapy.

These findings have been reduced to practice in methods and agents for assessing the function of a T-cell, for assessing the immune function of a subject, for predicting and/or monitoring response to therapy, for stratifying patients as likely responders or non-responders according to the form of EOMES expressed in the T-cell, for managing the treatment of patients according to the stratification, and for predicting clinical outcomes, as described hereafter.

In one aspect, therefore, provided is a method for assessing the function of a T-cell, the method comprising, consisting or consisting essentially of detecting in the T-cell a post-translational modification in the nuclear localization sequence and/or a DNA binding motif of EOMES.

In one embodiment, this method comprises detecting acetylation of EOMES-641K (also referred to herein as "EOMES-641K-Ac") in the T-cell and determining that the T-cell is dysfunctional. In a particular embodiment, an elevated level of EOMES-641K-Ac in the T-cell relative to a suitable control (e.g., a functional T-cell) is detected. The method may further comprise detecting the cellular localization (e.g. nuclear and/or cytoplasmic localization) of EOMES-641K-Ac in the T-cell. In a particular example, the method includes detecting the ratio of nuclear to cytoplasmic, or the ratio of cytoplasmic to nuclear, localization of EOMES-641K-Ac in the T-cell.

In a further embodiment of the method for assessing T-cell function, the method comprises detecting methylation of EOMES-641K (also referred to herein as "EOMES-641K-Me") in the T-cell and determining that the T-cell is functional. For example, an elevated level of EOMES-641K-Me in the T-cell relative to a suitable control (e.g., a dysfunctional T-cell) may be detected. The method may further include detecting the cellular localization (e.g. nuclear and/or cytoplasmic localization) of EOMES-641K-Me in the T-cell. In one example, the ratio of nuclear to cytoplasmic, or the ratio of cytoplasmic to nuclear, localization of EOMES-641K-Me in the T-cell is detected.

In another embodiment of the method for assessing T-cell function, the method comprises detecting methylation of EOMES-373K (also referred to herein as "EOMES-373K-Me") in the T-cell and determining that the T-cell is functional. In one example, an elevated level of EOMES-373K-Me in the T-cell relative to a suitable control (e.g., a dysfunctional T-cell) is detected. The method may further include detecting the cellular localization (e.g. nuclear and/or cytoplasmic localization) of EOMES-373K-Me in the T-cell. In one embodiment, the ratio of nuclear to cytoplasmic, or the ratio of cytoplasmic to nuclear, localization of EOMES-373K-Me in the T-cell is detected.

A further aspect of the invention provides a method for predicting the likelihood of response of a subject with cancer to a therapy (e.g., cytotoxic therapy and/or immunotherapy), the method comprising, consisting or consisting essentially of detecting in a T-cell or population of T-cells obtained from the subject a post-translational modification in the nuclear localization sequence of EOMES and/or in a DNA binding motif of EOMES, thereby predicting the likelihood of response of the subject to the therapy.

In one embodiment of this method, the method comprises detecting acetylation of EOMES-641K (also referred to herein as "EOMES-641K-Ac") in the T-cell or population of T-cells to thereby determine that the subject has increased likelihood of resistance or non-responsiveness to the therapy. In one example, the method includes detecting an elevated level of EOMES-641K-Ac in the T-cell or population of T-cells relative to a suitable control (e.g., a functional T-cell or a T-cell obtained from a healthy subject). The method may further comprise detecting the cellular localization (e.g. nuclear and/or cytoplasmic localization) of EOMES-641K-Ac in the T-cell. In a particular example, the method includes detecting the ratio of nuclear to cytoplasmic, or the ratio of cytoplasmic to nuclear, localization of EOMES-641K-Ac in the T-cell.

In a further embodiment of the method for predicting the likelihood of response of a subject with cancer to a therapy, the method comprises detecting methylation of EOMES-641K (also referred to herein as "EOMES-641K-Me") in the T-cell or population of T-cells to thereby determine that the subject has increased likelihood of sensitivity or responsiveness to the therapy. In one example, an elevated level of EOMES-641K-Me in the T-cell or population of T-cells relative to a suitable control (e.g., a dysfunctional T-cell) is detected. The method may further include detecting the cellular localization (e.g. nuclear and/or cytoplasmic localization) of EOMES-641K-Me in the T-cell. In one example the ratio of nuclear to cytoplasmic, or the ratio of cytoplasmic to nuclear, localization of EOMES-641K-Me in the T-cell is detected.

In another embodiment of the method for predicting the likelihood of response of a subject with cancer to a therapy, the method comprises detecting methylation of EOMES-373K (also referred to herein as "EOMES-373K-Me") in the T-cell or population of T-cells to thereby determine that the subject has increased likelihood of sensitivity or responsiveness to the therapy. In one example, an elevated level of EOMES-373K-Me in the T-cell or population of T-cells relative to a suitable control (e.g., a dysfunctional T-cell) is detected. The method can further comprise detecting the cellular localization (e.g. nuclear and/or cytoplasmic localization) of EOMES-373K-Me in the T-cell, and optionally detecting the ratio of nuclear to cytoplasmic, or the ratio of cytoplasmic to nuclear, localization of EOMES-373K-Me in the T-cell.

Another aspect of the invention relates to a method for determining likelihood of resistance of a subject with cancer to a therapy (e.g., cytotoxic therapy and/or immunotherapy), the method comprising, consisting or consisting essentially of detecting in a T-cell or population of T-cells obtained from the subject the presence of EOMES-641K-Ac, to thereby determine that the subject has increased likelihood of resistance to the therapy. In one embodiment, the method comprises detecting an elevated level of EOMES-641K-Ac in the T-cell or population of T-cells relative to a suitable control (e.g., a functional T-cell or a T-cell obtained from a healthy subject or subject who is sensitive to cancer therapy), which indicates that the subject has increased likelihood of resistance to the therapy. In a particular example, the method includes contacting a sample comprising the T-cell or population of T-cells with an antigen-binding molecule that binds specifically to EOMES-641K-Ac, and detecting in the sample a complex that comprises the antigen-binding molecule and EOMES-641K-Ac, to thereby determine that the subject has increased likelihood of resistance to the therapy.

Also provided is a method for determining likelihood of sensitivity of a subject with cancer to a therapy (e.g., cytotoxic therapy and/or immunotherapy), the method comprising, consisting or consisting essentially of detecting in a T-cell or population of T-cells obtained from the subject the presence of EOMES-641K-Me, to thereby determine that the subject has increased likelihood of sensitivity to the therapy. In one example, the method includes detecting an elevated level of EOMES-641K-Me in the T-cell or population of T-cells relative to a suitable control (e.g., a dysfunctional T-cell or a T-cell obtained from a subject who is resistant to cancer therapy), which indicates that the subject has increased likelihood of sensitivity to the therapy. In one particular embodiment, the method comprises contacting a sample comprising the T-cell or population of T-cells with an antigen-binding molecule that binds specifically to EOMES-641K-Me, and detecting in the sample a complex that comprises the antigen-binding molecule and the EOMES-641K-Me, to thereby determine that the subject has increased likelihood of sensitivity to the therapy.

In a further aspect, provided is a method for determining likelihood of sensitivity of a subject with cancer to a therapy (e.g., cytotoxic therapy and/or immunotherapy), the method comprising, consisting or consisting essentially of detecting in a T-cell or population of T-cells obtained from the subject the presence of EOMES-373K-Me, to thereby determine that the subject has increased likelihood of sensitivity to the therapy. In some examples, the method includes detecting an elevated level of EOMES-373K-Me in the T-cell or population of T-cells relative to a suitable control (e.g., a dysfunctional T-cell or a T-cell obtained from a subject who is resistant to cancer therapy), which indicates that the subject has increased likelihood of sensitivity to the therapy. In further examples, the method involves contacting a sample comprising the T-cell or population of T-cells with an antigen-binding molecule that binds specifically to EOMES-373K-Me, and detecting in the sample a complex that comprises the antigen-binding molecule and the EOMES-373K-Me, to thereby determine that the subject has increased likelihood of sensitivity to the therapy.

In another aspect, the invention provides a method for predicting a likelihood of response of a subject with cancer to a therapy (e.g., cytotoxic therapy and/or immunotherapy), the method comprising, consisting or consisting essentially of: measuring in a T-cell or population of T-cells obtained from the subject the level of EOMES-641K-Ac and EOMES-641K-Me; comparing the level of EOMES-641K-Ac and EOMES-641K-Me in the T-cell or population of T-cells; and predicting the response of the subject to the therapy based on the comparison, wherein a higher level of EOMES-641K-Ac than EOMES-641K-Me indicates that the subject has an increased likelihood of resistance to the therapy and wherein a higher level of EOMES-641K-Me than EOMES-641K-Ac indicates that the subject has an increased likelihood of sensitivity to the therapy. In one embodiment, the method includes contacting a sample comprising the T-cell or population of T-cells with a first antigen-binding molecule that binds specifically to EOMES-641K-Ac and a second antigen-binding molecule that binds specifically to EOMES-641K-Me; measuring in the sample the level of a first complex that comprises the first antigen-binding molecule and the EOMES-641K-Ac, and the level of a second complex that comprises the second antigen-binding molecule and the EOMES-641K-Me; and predicting the likelihood of response of the subject to the therapy based on the comparison, wherein a higher level of the first complex than the second complex in the sample indicates that the subject has an increased likelihood of resistance to the therapy and wherein a higher level of the second complex than the first complex in the sample indicates that the subject has an increased likelihood of sensitivity to the therapy. The method may further involve detecting in the T-cell or T-cell population at least one additional biomarker, such as IFN-γ, TNF-α, IL-2, Ki67, PD-1 and/or CD107a.

Also provided is a method for stratifying a subject with cancer as a likely responder or non-responder to a therapy (e.g., cytotoxic therapy and/or immunotherapy), the method comprising, consisting or consisting essentially of: detecting in a sample taken from the subject a T-cell or population of T-cells that comprises a post-translational modification in the nuclear localization sequence and/or DNA binding motif of EOMES, to thereby stratify the subject as a likely responder or non-responder to the therapy.

In one example, this method includes detecting EOMES-641K-Ac in the T-cell or population of T-cells and stratifying the subject as a likely non-responder to the therapy. In a particular embodiment, the method involves contacting the sample with an antigen-binding molecule that binds specifically to EOMES-641K-Ac, and detecting in the sample a complex that comprises the antigen-binding molecule and the EOMES-641K-Ac, to thereby stratify the subject as a likely non-responder to the therapy. In a further embodiment, the method comprises detecting EOMES-641K-Me in the T-cell or population of T-cells and stratifying the subject as a likely responder to the therapy, e.g. by contacting the sample with an antigen-binding molecule that binds specifically to EOMES-641K-Me, and detecting in the sample a complex that comprises the antigen-binding molecule and the EOMES-641K-Me, to thereby stratify the subject as a likely responder to the therapy. In another embodiment, the method comprises detecting EOMES-373K-Me in the T-cell or population of T-cells and stratifying the subject as a likely responder to the therapy, e.g. by contacting the sample with an antigen-binding molecule that binds specifically to EOMES-373K-Me, and detecting in the sample a complex that comprises the antigen-binding molecule and the EOMES-373K-Me, to thereby stratify the subject as a likely responder to the therapy.

In one embodiment of the method for stratifying a subject with cancer as a likely responder or non-responder to a therapy, the method includes contacting the sample with a first antigen-binding molecule that binds specifically to EOMES-641K-Ac and a second antigen-binding molecule that binds specifically to EOMES-641K-Me; measuring in the sample the level of a first complex that comprises the first antigen-binding molecule and EOMES-641K-Ac, and the level of a second complex that comprises the second antigen-binding molecule and EOMES-641K-Me; and stratifying the subject as a likely responder or non-responder based on the comparison, wherein the subject is stratified as a likely non-responder if the level of the first complex is higher than the second complex in the sample and wherein the subject is stratified as a likely responder if the level of the second complex is higher than the first complex in the sample.

Also provided is a method for managing treatment of a subject with cancer with a therapy (e.g., cytotoxic therapy and/or immunotherapy), the method comprising, consisting or consisting essentially of: selecting a subject with cancer for treating with the therapy on the basis that the subject is a likely responder to the therapy, or selecting a subject with cancer for not treating with the therapy on the basis that the subject is a likely non-responder to the therapy and treating or not treating the subject with the therapy based on the selection, wherein the selection is based on a stratification method that comprises detecting in a sample taken from the subject a T-cell or population of T-cells that comprises a post-translational modification in the nuclear localization sequence and/or a DINA binding motif of EOMES, to thereby stratify the subject as a likely responder or non-responder to the therapy. In one example, the stratification method comprises detecting EOMES-641K-Me in the T-cell or population of T-cells and stratifying the subject as a likely responder to the therapy, e.g. by contacting the sample with an antigen-binding molecule that binds specifically to EOMES-641K-Me, and detecting in the sample a complex that comprises the antigen-binding molecule and the EOMES-641K-Me, to thereby stratify the subject as a likely responder to the therapy. In another example, the stratification method comprises detecting EOMES-373K-Me in the T-cell or population of T-cells and stratifying the subject as a likely responder to the therapy, e.g. by contacting the sample with an antigen-binding molecule that binds specifically to EOMES-373K-Me, and detecting in the sample a complex that comprises the antigen-binding molecule and the EOMES-373K-Me, to thereby stratify the subject as a likely responder to the therapy. In a further example, the stratification method comprises detecting EOMES-641K-Ac in the T-cell or T-cell population and stratifying the patient as a likely non-responder to the therapy, e.g. by contacting the sample with an antigen-binding molecule that binds specifically to EOMES-641K-Ac, and detecting in the sample a complex that comprises the antigen-binding molecule and the EOMES-641K-Ac, to thereby stratify the patient as a likely non-responder to the therapy. In a particular embodiment, the stratification method comprises contacting the sample with a first antigen-binding molecule that binds specifically to EOMES-641K-Ac and a second antigen-binding molecule that binds specifically to PD EOMES-641K-Me; measuring in the sample the level of a first complex that comprises the first antigen-binding molecule and EOMES-641K-Ac, and the level of a second complex that comprises the second antigen-binding molecule and EOMES-641K-Me; and stratifying the subject as a likely responder or non-responder based on the comparison, wherein the subject is stratified as a likely non-responder if the level of the first complex is higher than the second complex in the sample and wherein the subject is stratified as a likely responder if the level of the second complex is higher than the first complex in the sample.

In some examples of the above methods, the methods further comprise detecting at least one additional biomarker in the T-cell or population of T-cells, such as, for example, IFN-γ, TNF-α; IL-2, Ki67, PD-1 and/or CD107a.

In a further aspect, provided is a method for assessing the immune function of a subject, the method comprising, consisting or consisting essentially of detecting in a T-cell or population of T-cells obtained from the subject a post-translational modification in the nuclear localization sequence of EOMES and/or in a DNA binding motif of EOMES.

In one embodiment, the method involves detecting acetylation of EOMES-641K (also referred to herein as "EOMES-641K-Ac") in the T-cell or population of T-cells to thereby determine that the subject has impaired immune function. For example, the method may comprise detecting an elevated level of EOMES-641K-Ac in the T-cell or population of T-cells relative to a suitable control (e.g., a T-cell obtained from a subject with normal or competent immune function). In some embodiments, the cellular localization of EOMES-641K-Ac in the T-cell is detected, e.g. the nuclear and/or cytoplasmic localization. In a particular example, the method includes detecting the ratio of nuclear to cytoplasmic, or the ratio of cytoplasmic to nuclear, localization EOMES-641K-Ac in the T-cell.

In a further embodiment, the method for assessing immune function includes detecting methylation of EOMES-641K (also referred to herein as "EOMES-641K-Me") in the T-cell or population of T-cells to thereby determine that the subject has normal or competent immune function, e.g. detecting an elevated level of EOMES-641K-Me in the T-cell or population of T-cells relative to a suitable control (e.g., a T-cell from a subject with impaired immune function). In one example, the cellular localization of EOMES-641K-Me in the T-cell is detected, e.g. the nuclear and/or cytoplasmic localization. In a particular example, the method involves detecting the ratio of nuclear to cytoplasmic, or the ratio of cytoplasmic to nuclear, localization of EOMES-641K-Me in the T-cell.

In another embodiment, the method comprises detecting methylation of EOMES-373K (also referred to herein as "EOMES-373K-Me") in the T-cell or population of T-cells to thereby determine that the subject has a normal or competent immune function, e.g. detecting an elevated level of EOMES-373K-Me in the T-cell or population of T-cells relative to a suitable control (e.g., a T-cell from a subject with impaired immune function). In one embodiment, the method comprises detecting the cellular localization of EOMES-373K-Me in the T-cell, e.g. detecting nuclear and/or cytoplasmic localization of EOMES-373K-Me in the T-cell, and optionally detecting the ratio of nuclear to cytoplasmic, or the ratio of cytoplasmic to nuclear, localization EOMES-373K-Me in the T-cell.

Also provided is an antigen-binding molecule that binds specifically to EOMES-641K-Ac, suitably for assessing the function of a T-cell, for predicting the likelihood of response of a subject with cancer to a therapy (e.g., cytotoxic therapy and/or immunotherapy), for determining likelihood of resistance of a subject with cancer to a therapy (e.g., cytotoxic therapy and/or immunotherapy), for determining likelihood of sensitivity of a subject with cancer to a therapy (e.g., cytotoxic therapy and/or immunotherapy), for stratifying a subject with cancer as a likely responder or non-responder to a therapy (e.g., cytotoxic therapy and/or immunotherapy), for managing treatment of a subject with cancer with a therapy (e.g., cytotoxic therapy and/or immunotherapy), for assessing the immune function of a subject and/or for managing treatment of a subject having impaired or reduced immune function with a therapy (e.g., immunotherapy).

In another aspect, provided is a complex comprising EOMES-641K-Ac and an antigen-binding molecule that binds specifically to the EOMES-641K-Ac.

In a further aspect, provided is an antigen-binding molecule that binds specifically to EOMES-641K-Me, suitably for assessing the function of a T-cell, for predicting the likelihood of response of a subject with cancer to a therapy (e.g., cytotoxic therapy and/or immunotherapy), for determining likelihood of resistance of a subject with cancer to a therapy (e.g., cytotoxic therapy and/or immunotherapy), for determining likelihood of sensitivity of a subject with cancer to a therapy (e.g., cytotoxic therapy and/or immunotherapy), for stratifying a subject with cancer as a likely responder or non-responder to a therapy (e.g., cytotoxic therapy and/or immunotherapy), for managing treatment of a subject with cancer with a therapy (e.g., cytotoxic therapy and/or immunotherapy), for assessing the immune function of a subject and/or for managing treatment of a subject having impaired or reduced immune function with a therapy (e.g., immunotherapy).

Also described herein is a complex comprising EOMES-641K-Me and an antigen-binding molecule that binds specifically to the EOMES-641K-Me.

In another aspect, provided is an antigen-binding molecule that binds specifically to EOMES-373K-Me, suitably for assessing the function of a T-cell, for predicting the likelihood of response of a subject with cancer to a therapy (e.g., cytotoxic therapy and/or immunotherapy), for determining likelihood of resistance of a subject with cancer to a therapy (e.g., cytotoxic therapy and/or immunotherapy), for determining likelihood of sensitivity of a subject with cancer to a therapy (e.g., cytotoxic therapy and/or immunotherapy), for stratifying a subject with cancer as a likely responder or non-responder to a therapy (e.g., cytotoxic therapy and/or immunotherapy), for managing treatment of a subject with cancer with a therapy (e.g., cytotoxic therapy and/or immunotherapy), for assessing the immune function of a subject and/or for managing treatment of a subject having impaired or reduced immune function with a therapy (e.g., immunotherapy).

Also provided is a complex comprising EOMES-373K-Me and an antigen-binding molecule that binds specifically to the EOMES-373K-Me.

A further aspect of the invention provides a kit for assessing the function of a T-cell, for predicting the likelihood of response of a subject with cancer to a therapy (e.g., cytotoxic therapy and/or immunotherapy), for determining likelihood of resistance of a subject with cancer to a therapy (e.g., cytotoxic therapy and/or immunotherapy), for determining likelihood of sensitivity of a subject with cancer to a therapy (e.g., cytotoxic therapy and/or immunotherapy), for stratifying a subject with cancer as a likely responder or non-responder to a therapy (e.g., cytotoxic therapy and/or immunotherapy), for managing treatment of a subject with cancer with a therapy (e.g., cytotoxic therapy and/or immunotherapy) for assessing the immune function of a subject and/or for managing treatment of a subject having impaired or reduced immune function with a therapy (e.g., immunotherapy), which kit includes at least 1, 2 or each of an antigen-binding molecule that binds specifically to EOMES-641K-Ac, an antigen-binding molecule that binds specifically to EOMES-641K-Me and an antigen-binding molecule that binds specifically to EOMES-373K-Me. In one embodiment, the kit further comprises one or more controls including positive and negative controls, e.g, wherein the positive control is selected from a EOMES-641K-Ac polypeptide, a EOMES-641K-Me polypeptide and an EOMES-373K-Me polypeptide. The kit may optionally include instructional material for performing a method described above and herein.

Another aspect of the invention relates to a T-cell that comprises a complex comprising EOMES-641K-Ac and a first antigen-binding molecule that binds specifically to EOMES-641K-Ac; EOMES-641K-Me and a first antigen-binding molecule that binds specifically to EOMES-641K-Me; or an EOMES-373-Me and first antigen-binding molecule that binds specifically to EOMES-373K-Me. In one example, the T-cell further comprises an second antigen-binding molecule that binds to the first antigen-binding molecule, e.g. a second antigen-binding molecule that comprises a detectable label.

In one embodiment of the method, kit, antigen-binding molecule, complex or T-cell described above and herein, the therapy is an immunotherapy, such as an immune checkpoint inhibitor. Exemplary inhibitors include antagonist antigen-binding molecules (e.g., antibody) that bind specifically to an immune checkpoint molecule. In one example, the antagonist antigen-binding molecule (e.g., antibody) binds specifically to an immune checkpoint molecule selected from PD-1, PD-L1 and CTLA4.

DETAILED DESCRIPTION OF THE INVENTION

1. Definitions

Figure 1:
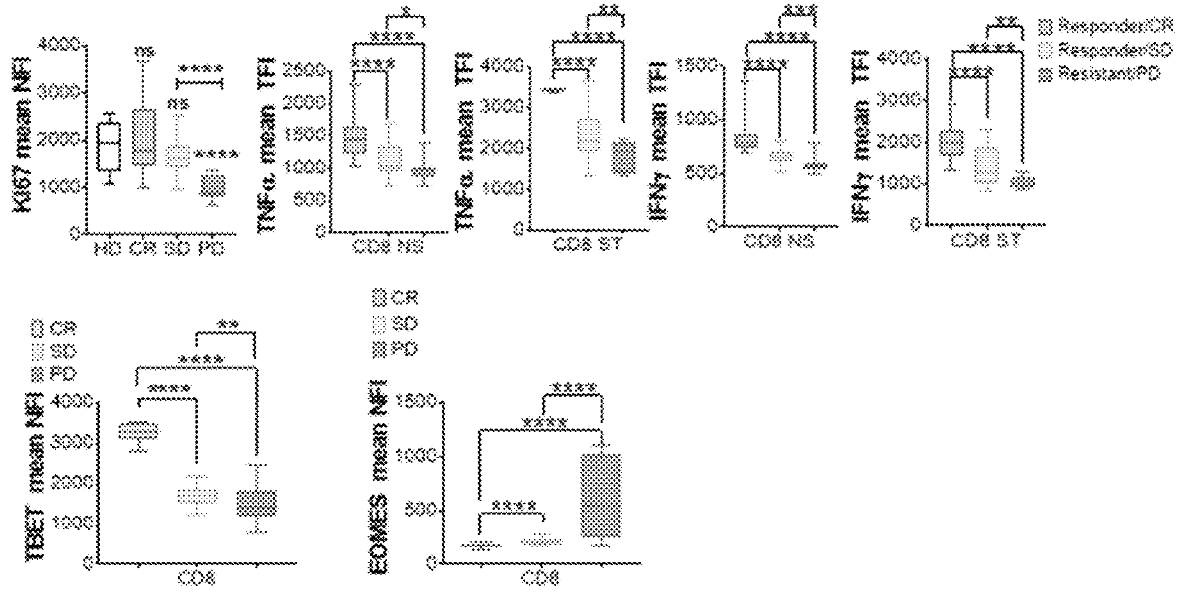
FIG. 1 is a schematic, graphical and photographic representation showing prevalence of EOMES in CD8+ T-cells isolated from healthy donors and patients with metastatic breast cancer or melanoma. CD8+ T-cells were isolated from liquid biopsies of healthy donors (HD), patients with metastatic breast cancer or patients with melanoma every 3 months for 24 months after a baseline bleed. Melanoma patients were further classified based on objective response to immunotherapy treatment (either mono or dual therapy using Pembrolizumab, Nivolumab and/or Ipilimumab) into complete response (CR), partial response (PR), stable disease (SD) or progressive disease (PD). The depicted plot shows the % change in tumour growth as described for RECIST 1.1 for either PD (progressive disease) or CR (complete response) patient cohorts. (A) CD8+ T-cells were isolated from complete response (CR), stable disease (SD) or progressive disease (PD) melanoma patients as described above. Cells were stimulated with phorbol-12-myristate 13-acetate plus calcium ionophore A23187 (PMA/CI) or non-stimulated then fixed. Immunofluorescence microscopy was performed with primary antibodies to anti-Ki67 for NS $CD8^+$ T-Cells and anti-TNF-α or anti-IFN-γ for NS or ST $CD8^+$ T-cells with DAPI staining. The graphs represents the Nuclear Fluorescent Intensity (NFI) values for Ki67 and the Total Fluorescent Intensity (TFI) values for TNF-α and IFN-γ, and were measured using ImageJ to select the nucleus minus background (n>20 individual cells per a patient for 10 patients a cohort). (B) $CD8^+$ T-cells were isolated from healthy donors (HD) and melanoma patients classified as complete response (CR), partial response (PR), stable disease (SD) or progressive disease (PD) as described above. Cells were fixed and immunofluorescence microscopy was performed with primary antibodies to EOMES and PD1 with DAPI staining. The graphs represent the NFI values for the complex of EOMES and mean TFI for PD-1, and were measured using a generic scan and analysis system (Applied Scientific Instrumentation; ASI) for multiplexed immunofluorescent samples for high through-put IF microscopy to quantify cell number and IF signal intensity (n>2500 individual cells per a patient for 10 patients a cohort). Graph represents % population. (D) EOMES protein structure showing the NLS domain. (D) Schematic of EOMES plasmids: EOMES WT (E-WT; wild type EOMES); EOMES Mutant 1 (E-MUT1; EOMES with an alanine mutation at the lysine at position 641, which mimics a non-acetylation or non-methylation of the lysine residue); and EOMES Mutant 2 (E-MUT2; EOMES with a phenylalanine mutation at the lysine at position 641, which mimics a hyper-methylation state of the lysine residue). (E) Jurkat T-cells were transfected with either vector only (VO), E-WT, E-MUT1 or E-MUT2 and were probed with an anti-EOMES, anti-TBET and anti-PD1 antibody. Graph plots represent the Fn/c of EOMES or the mean NFI of EOMES, or mean TFI of PD-1, measured using ImageJ minus background (n=>20 cells per a group). Representative images for each dataset are shown. Scale bar is shown in orange and is equal to 10 mm in length. (F) Jurkat T-cells transfected with either VO, E-WT, E-MUT1 or E-MUT2 were probed with an anti-Ki67, anti-IFN-γ and anti-TNF-α antibody. Graph plots represent the TFI of Ki67, IFN-γ and -TNF-α measured using ImageJ minus background (n=>20 cells per a group).
Figure 1:
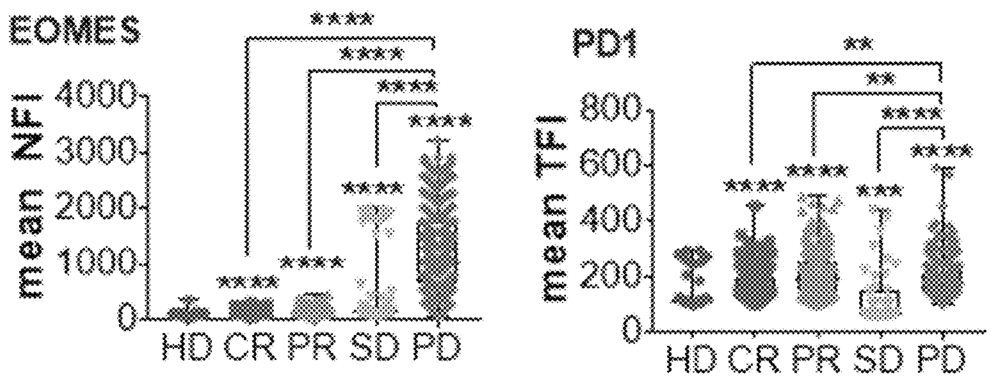
Figure 1:
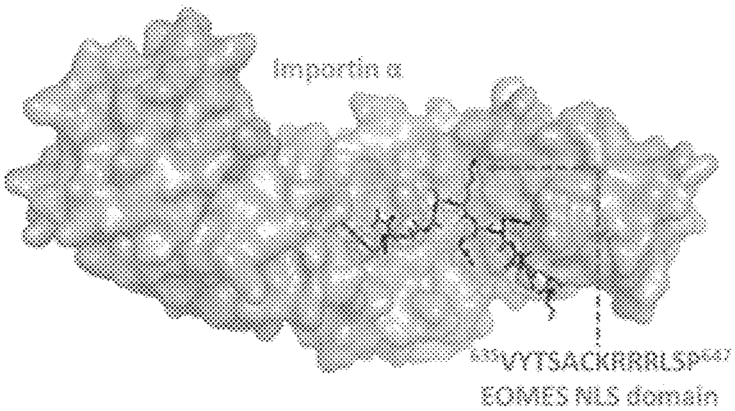
Figure 1:
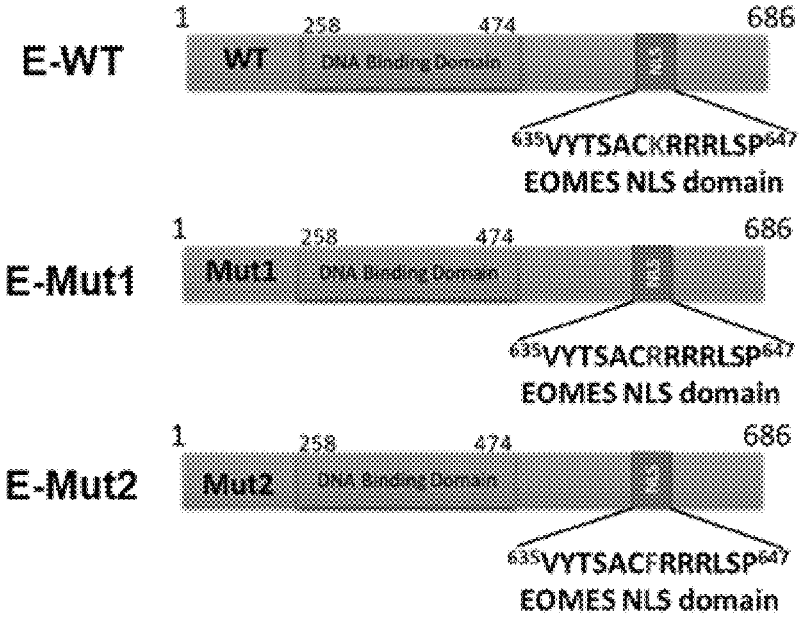
Figure 1:
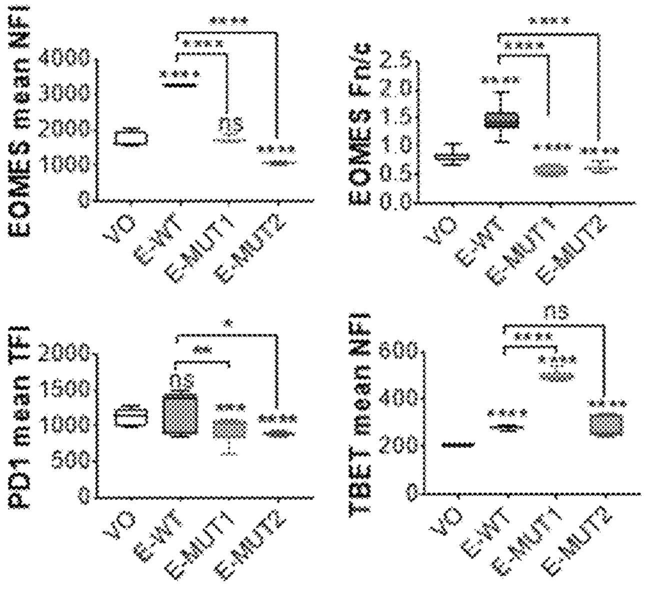
Figure 1:
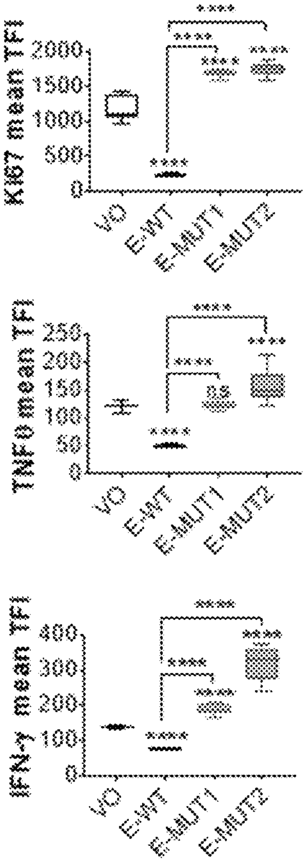

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

The term "about" as used herein refers to the usual error range for the respective value readily known to the skilled person in this technical field. Reference to "about" a value or parameter herein includes (and describes) embodiments that are directed to that value or parameter per se.

The terms "administration concurrently" or "administering concurrently" or "co-administering" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and desirably together in the same formulation. By "contemporaneously" it is meant that the active agents are administered closely in time, e.g., one agent is administered within from about one minute to within about one day before or after another. Any contemporaneous time is useful. However, it will often be the case that when not administered simultaneously, the agents will be administered within about one minute to within about eight hours and suitably within less than about one to about four hours. When administered contemporaneously, the agents are suitably administered at the same site on the subject. The term "same site" includes the exact location, but can be within about 0.5 to about 15 centimeters, preferably from within about 0.5 to about 5 centimeters. The term "separately" as used herein means that the agents are administered at an interval, for example at an interval of about a day to several weeks or months. The active agents may be administered in either order. The term "sequentially" as used herein means that the agents are administered in sequence, for example at an interval or intervals of minutes, hours, days or weeks. If appropriate the active agents may be administered in a regular repeating cycle.

The term "agent" refers to any diagnostic, therapeutic, or preventative agents. The term "agent" is not to be construed narrowly but extends to small molecules, proteinaceous molecules such as peptides, polypeptides and proteins as well as genetic molecules such as RNA, DNA and mimetics and chemical analogs thereof as well as cellular agents. The term "agent" includes a cell that is capable of producing and secreting a polypeptide referred to herein as well as a polynucleotide comprising a nucleotide sequence that encodes that polypeptide. The term "agent" also extends to nucleic acid constructs including vectors such as viral or non-viral vectors, expression vectors and plasmids for expression in and secretion in a range of cells.

"Amplification," as used herein generally refers to the process of producing multiple copies of a desired sequence. "Multiple copies" mean at least two copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification;

The "amount" or "level" of a biomarker is a detectable level or amount in a sample. These can be measured by methods known to one skilled in the art and also disclosed herein. These terms encompass a quantitative amount or level (e.g., weight or moles), a semi-quantitative amount or level, a relative amount or level (e.g., weight % or mole % within class), a concentration, and the like. Thus, these terms encompass absolute or relative amounts or levels or concentrations of a biomarker in a sample. The expression level or amount of biomarker assessed can be used to determine the response to treatment.

As used herein, "and/or" refers to and encompasses any and all possible combinations of one or more of the associated listed items, as well as the lack of combinations when interpreted in the alternative (or).

The term "antagonist" or "inhibitor" refers to a substance that prevents, blocks, inhibits, neutralizes, or reduces a biological activity or effect of another molecule, such as a receptor.

The term "antagonist antibody" refers to an antibody that binds to a target and prevents or reduces the biological effect of that target. In some embodiments, the term can denote an antibody that prevents the target, e.g., PD-1. CTLA4 etc., to which it is bound from performing a biological function.

As used herein, an "anti-immune check point molecule antagonist antibody" refers to an antibody that is able to inhibit the biological activity and/or downstream events(s) mediated by an immune check point molecule. Anti-immune check point molecule antagonist antibodies encompass antibodies that block, antagonize, suppress or reduce (to any degree including significantly) immune check point molecule biological activity, including inhibitory signal transduction through the immune check point molecule and downstream events mediated by the immune check point molecule, such as binding and downstream signaling of an immune check point molecule binding partner to the immune check point molecule, inhibition of cell proliferation, including tumor proliferation, inhibition of T-cell proliferation, inhibition of T-cell activation, inhibition of cytokine secretion and inhibition of anti-tumor immune responses. For purposes of the present invention, it will be explicitly understood that the term "anti-immune check point molecule antagonist antibody" (interchangeably termed "antagonist immune check point molecule antibody", "antagonist anti-immune check point molecule antibody" or "immune check point molecule antagonist antibody") encompasses all the previously identified terms, titles, and functional states and characteristics whereby the immune check point molecule itself, a biological activity of the immune check point molecule, or the consequences of the biological activity, are substantially nullified, decreased, or neutralized in any meaningful degree.

The term "antibody" herein is used in the broadest sense and specifically covers monoclonal antibodies (including full length monoclonal antibodies), polyclonal antibodies, chimeric antibodies, humanized antibodies, human antibodies, multispecific antibodies (e.g., bispecific antibodies), and single variable domain antibodies so long as they exhibit the desired biological activity. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (which may be abbreviated as HCVR or $V_H$) and a heavy chain constant region. The heavy chain constant region comprises three domains, $C_{H1}$, $C_{H2}$ and $C_{H3}$. Each light chain comprises a light chain variable region (which may be abbreviated as LCVR or $V_L$) and a light chain constant region. The light chain constant region comprises one domain ($C_{L1}$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of an antibody (or antigen-binding portion thereof) may be identical to the human germline sequences, or may be naturally or artificially modified. An amino acid consensus sequence may be defined based on a side-by-side analysis of two or more CDRs. Included within the scope of the term "antibody" is an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called α, δ, ε, γ, and μ, respectively. The subunit structures and three-dimensional configurations of different classes of immunoglobulins are well known.

An "antigen-binding fragment" may be provided by means of arrangement of one or more CDRs on non-antibody protein scaffolds. "Protein Scaffold" as used herein includes but is not limited to an immunoglobulin (Ig) scaffold, for example an IgG scaffold, which may be a four chain or two chain antibody, or which may comprise only the Fc region of an antibody, or which may comprise one or more constant regions from an antibody, which constant regions may be of human or primate origin, or which may be an artificial chimera of human and primate constant regions. The protein scaffold may be an Ig scaffold, for example an IgG, or IgA scaffold. The IgG scaffold may comprise some or all the domains of an antibody (i.e. CH1, CH2, CH3, $V_H$, $V_L$). The antigen binding protein may comprise an IgG scaffold selected from IgG1, IgG2, IgG3, IgG4 or IgG4PE. For example, the scaffold may be IgG1. The scaffold may consist of, or comprise, the Fc region of an antibody, or is a part thereof. Non-limiting examples of antigen-binding fragments include: (i) Fab fragments; (ii) F(ab') 2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment," as used herein. An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain. In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_{H1}$; (ii) $V_H$-$C_{H2}$; (iii) $V_H$-$C_{H3}$; (iv) $V_H$-$C_{H1}$-$C_{H2}$; (v) $V_H$-$C_{H1}$-$C_{H2}$-$C_{H3}$, (vi) $V_H$-$C_{H2}$-$C_{H3}$; (VII) $V_H$-$C_L$; (viii) $V_L$-$C_{H1}$; (ix) $V_L$-$C_{H2}$, (x) $V_L$-$C_{H3}$; (xi) $V_L$-$C_{H1}$-$C_{H2}$; (xii) $V_L$-$C_{H1}$-$C_{H2}$-$C_{H3}$; (xiii) $V_L$-$C_{H2}$-$C_{H3}$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)). As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antigen-binding molecule format, including the exemplary bispecific antigen-binding molecule formats disclosed herein, may be adapted for use in the context of an antigen-binding fragment of an antibody of the present invention using routine techniques available in the art.

As used herein, the term "antigen" and its grammatically equivalents expressions (e.g., "antigenic") refer to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity. Representative antigen-binding molecules that are useful in the practice of the present invention include antibodies and antigen-binding fragments.

The term "antigen-presenting cell" or "APC" refers to refers to a class of cells capable of presenting one or more antigens in the form of peptide-MHC complex recognizable by specific effector cells of the immune system (also referred to herein as "immune effector cells"), and thereby modulating (e.g., stimulating/enhancing or reducing/tolerizing/anergizing) an immune response to the antigen or antigens being presented. In specific embodiments of the present invention, the APCs are capable of activating immune effector cells such as T lymphocytes, including $CD8^+$ and/or $CD4^+$ lymphocytes. Cells that have in vivo the potential to act as APC include, for example, not only professional APCs such as dendritic cells, macrophages, Langerhans cell, monocytes and B cells but also non-professional APCs illustrative examples of which include activated epithelial cells, fibroblasts, glial cells, pancreatic beta cells and vascular endothelial cells, as well as cancer cells. Many types of cells are capable of presenting antigens on their cell surface for immune effector cell, including T-cell, recognition.

As used herein, the term "antigen-specific" refers to a property of a cell population such that supply of a particular antigen, or a fragment of the antigen, results in specific cell proliferation, suitably T-cell proliferation characterized for example by activation of the T-cells (e.g., CTLs and/or helper T-cells) that are suitably directed against a damaged cell, malignancy or infection.

As use herein, the term "binds", "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 μM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

The term "biomarker" as used herein refers to an indicator, e.g., predictive, diagnostic, and/or prognostic, which can be detected in a sample. The biomarker may serve as an indicator of a particular subtype of a disease or disorder (e.g., cancer), characterized by certain, molecular, pathological, histological, and/or clinical features, and/or may serve as an indicator of a particular cell type or state (e.g., epithelial, mesenchymal etc.) and/or or response to therapy. Biomarkers include, but are not limited to, polynucleotides (e.g., DNA, and/or RNA), polynucleotide copy number alterations (e.g., DNA copy numbers), polypeptides, polypeptide and polynucleotide modifications (e.g., posttranslational modifications), carbohydrates, and/or glycolipid-based molecular markers. A biomarker may be present in a sample obtained from a subject before the onset of a physiological or pathophysiological state (e.g., primary cancer, metastatic cancer, etc.), including a symptom, thereof (e.g., response to therapy). Thus, the presence of the biomarker in a sample obtained from the subject can be indicative of an increased risk that the subject will develop the physiological or pathophysiological state or symptom thereof. Alternatively, or in addition, the biomarker may be normally expressed in an individual, but its expression may change (i.e., it is increased (upregulated; over-expressed) or decreased (downregulated; under-expressed) before the onset of a physiological or pathophysiological state, including a symptom thereof. Thus, a change in the level of the biomarker may be indicative of an increased risk that the subject will develop the physiological or pathophysiological state or symptom thereof. Alternatively, or in addition, a change in the level of a biomarker may reflect a change in a particular physiological or pathophysiological state, or symptom thereof, in a subject, thereby allowing the nature (e.g., severity) of the physiological or pathophysiological state, or symptom thereof, to be tracked over a period of time. This approach may be useful in, for example, monitoring a treatment regimen for the purpose of assessing its effectiveness (or otherwise) in a subject. As herein described, reference to the level of a biomarker includes the concentration of a biomarker, or the level of expression of a biomarker, or the activity of the biomarker.

The terms "biomarker signature", "signature", "biomarker expression signature", or "expression signature" are used interchangeably herein and refer to one or a combination of biomarkers whose expression is an indicator, e.g., predictive, diagnostic, and/or prognostic. The biomarker signature may serve as an indicator of a particular subtype of a disease or disorder (e.g., primary cancer, metastatic cancer, etc.) or symptom thereof (e.g., response to therapy, drug resistance, and/or disease burden) characterized by certain molecular, pathological, histological, and/or clinical features. In some embodiments, the biomarker signature is a "gene signature." The term "gene signature" is used interchangeably with "gene expression signature" and refers to one or a combination of polynucleotides whose expression is an indicator, e.g., predictive, diagnostic, and/or prognostic. In some embodiments, the biomarker signature is a "protein signature." The term "protein signature" is used interchangeably with "protein expression signature" and refers to one or a combination of polypeptides whose expression is an indicator, e.g., predictive, diagnostic, and/or prognostic. A biomarker signature may comprise at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 or more biomarkers.

The terms "cancer" and "cancerous" refer to or describe the physiological condition in subjects that is typically characterized by unregulated cell growth, with potential to invade locally and/or spread to other parts of the body (metastasize). The term "cancer" is generally used interchangeably with "tumor" herein (unless a tumor is specifically referred to as a "benign" tumor, which is an abnormal mass of cells that lacks the ability to invade neighboring tissue or metastasize), and encompasses malignant solid tumors (e.g., carcinomas, sarcomas) and malignant growths in which there may be no detectable solid tumor mass (e.g., certain hematologic malignancies). Non-limiting examples of cancers include but are not limited to, carcinoma, lymphoma, blastoma, sarcoma, and leukemia or lymphoid malignancies. More particular examples of such cancers include, but not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phacomatoses, edema (such as that associated with brain tumors), Meigs' syndrome, brain, as well as head and neck cancer, and associated metastases. In certain embodiments, cancers that are amenable to treatment by the antibodies of the invention include breast cancer, colorectal cancer, rectal cancer, non-small cell lung cancer, glioblastoma, non-Hodgkin's lymphoma (NHL), renal cell cancer, prostate cancer, liver cancer, pancreatic cancer, soft-tissue sarcoma, Kaposi's sarcoma, carcinoid carcinoma, head and neck cancer, ovarian cancer, mesothelioma, and multiple myeloma. In some embodiments, the cancer is selected from: small cell lung cancer, glioblastoma, neuroblastomas, melanoma, breast carcinoma, gastric cancer, colorectal cancer (CRC), and hepatocellular carcinoma. Yet in some embodiments, the cancer is selected from: non-small cell lung cancer, colorectal cancer, glioblastoma and breast carcinoma, including metastatic forms of those cancers. In specific embodiments, the cancer is melanoma or lung cancer, suitably metastatic melanoma or metastatic lung cancer.

The term "cellular compartment" includes a part of a cell including organelles (such as mitochondria, Golgi apparatus, endoplasmic reticulum, ribosomes, etc.), the nucleus, the cytoplasm (optionally including the organelles), the nuclear membrane, the cell membrane and other cellular regions.

The term "chemotherapy" refers to a therapy of a human or animal with one or more chemotherapeutic agents, which inhibit or abrogate cell growth and cell division, namely, the therapy is taken as a cell proliferation inhibitor or is used for inducing cell death (cell apoptosis). Compared with normal cells, cancer cells grow and divide uncontrollably so that the chemotherapy should be more effective to the cancer cells.

The term "chemotherapeutic agent" refers to chemical compounds that are effective in inhibiting tumor growth. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4 (5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-α, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length $IgG_1$ λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al., Eur. J. Cancer 32A: 636-640 (1996)); EMD7200 (matuzumab) a humanized EGFR antibody directed against EGFR that competes with both EGF and TGF-α for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., J. Biol. Chem. 279 (29): 30375-30384 (2004)). The anti-EGFR antibody may be conjugated with a cytotoxic agent, thus generating an immunoconjugate (see, e.g., EP659439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quin-azolinyl]-, dihydrochloride, Pfizer Inc.); ZD1839, gefitinib (IRESSA®) 4-(3'-Chloro-4'-fluoroanilino)-7-methoxy-6-(3-morpholinopropoxy) quinazoli-ne, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol)-; (R)-6-(4-hydroxyphenyl)-4-[(1-phenylethyl)amino]-7H-pyrrolo[2,3-d]pyrimi-dine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(-dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl) methoxy]phenyl]-6[5[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino) phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor α (TNF-α) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T-cell costimulation blockers such as abatacept (Orencia), Interleukin 6 (IL-6) blockers such as tocilizumab (ACTEMERA®); Interleukin 13 (IL-13) blockers such as lebrikizumab; Interferon α (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/B2 blockers such as Anti-lymphotoxin α (LTa); radioactive isotopes (e.g., At211, 1131, I125, Y90, Re186, Re188, Sm153, Bi212, P32, Pb212 and radioactive isotopes of Lu); miscellaneous investigational agents such as thioplatin, PS-341, phenylbutyrate, ET-18-$OCH_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhea, metastatic bone pain, headache and migraine, postoperative pain, mild-to-moderate pain due to inflammation and tissue injury, pyrexia, ileus, and renal colic.

The term "clinical outcome" or "clinical endpoint" refers to any clinical observation or measurement relating to a patient's reaction to a therapy. Non-limiting examples of clinical outcomes include tumor response (TR), overall survival (OS), progression free survival (PFS), disease free survival (DFS), time to tumor recurrence (TTR), time to tumor progression (TTP), relative risk (RR), toxicity or side effect. "Overall Survival" (OS) intends a prolongation in life expectancy as compared to naïve or untreated individuals or patients. "Progression free survival" (PFS) or "Time to tumor progression" (TTP) indicates the length of time during and after treatment that the cancer does not grow. Progression-free survival includes the amount of time patients have experienced a complete response or a partial response, as well as the amount of time patients have experienced stable disease. "Tumor recurrence" as used herein and as defined by the National. Cancer Institute is cancer that has recurred (come back), usually after a period of time during which the cancer could not be detected. The cancer may come back to the same place as the original (primary) tumor or to another place in the body. It is also called recurrent cancer. "Time to tumor recurrence" (TTR) is defined as the time from the date of diagnosis of the cancer to the date of first recurrence, death, or until last contact if the patient was free of any tumor recurrence at the time of last contact. If a patient had not recurred, then TTR was censored at the time of death or at the last follow-up. "Relative risk" (RR), in statistics and mathematical epidemiology, refers to the risk of an event (or of developing a disease) relative to exposure. Relative risk is a ratio of the probability of the event occurring in the exposed group versus a non-exposed group.

As used herein, the term "complex" refers to an assemblage or aggregate of molecules (e.g., peptides, polypeptides, etc.) in direct and/or indirect contact with one another. In specific embodiments, "contact", or more particularly, "direct contact" means two or more molecules are close enough so that attractive noncovalent interactions, such as Van der Waal forces, hydrogen bonding, ionic and hydrophobic interactions, and the like, dominate the interaction of the molecules. In such embodiments, a complex of molecules (e.g., a peptide and polypeptide) is formed under conditions such that the complex is thermodynamically favored (e.g., compared to a non-aggregated, or non-complexed, state of its component molecules). The term "polypeptide complex" or "protein complex," as used herein, refers to a trimer, tetramer, pentamer, hexamer, heptamer, octamer, nonamer, decamer, undecamer, dodecamer, or higher order oligomer. In specific embodiments, the polypeptide complexes are formed by binding of EOMES with an antigen-binding molecule specific for EOMES.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, the term "correlates" or "correlates with" and like terms, refers to a statistical association between two or more things, such as events, characteristics, outcomes, numbers, data sets, etc., which may be referred to as "variables". It will be understood that the things may be of different types. Often the variables are expressed as numbers (e.g., measurements, values, likelihood, risk), wherein a positive correlation means that as one variable increases, the other also increases, and a negative correlation (also called anti-correlation) means that as one variable increases, the other variable decreases.

By "corresponds to" or "corresponding to" is meant an amino acid sequence that displays substantial sequence similarity or identity to a reference amino acid sequence. In general the amino acid sequence will display at least about 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence similarity or identity to at least a portion of the reference amino acid sequence.

The term "cytotoxic agent" as used herein refers to any agent that is detrimental to cells (e.g., causes cell death, inhibits proliferation, or otherwise hinders a cellular function). Cytotoxic agents include, but are not limited to, radioactive isotopes (e.g., At211, 131, 1125, Y90, Re186, Re18, Sm153, Bi212, p32, Pb212 and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof. Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism. In some embodiments, the cytotoxic agent is a taxane. In representative examples of this type, the taxane is paclitaxel or docetaxel. In some embodiments, the cytotoxic agent is a platinum agent. In some embodiments, the cytotoxic agent is an antagonist of EGFR. In representative examples of this type, the antagonist of EGFR is N-(3-ethynylphenyl)-6,7-bis(2-methoxyethoxy) quinazolin-4-amine (e.g., erlotinib). In some embodiments, the cytotoxic agent is a RAF inhibitor. In non-limiting examples of this type, the RAF inhibitor is a BRAF and/or CRAF inhibitor. In other non-limiting examples, the RAF inhibitor is vemurafenib. In one embodiment the cytotoxic agent is a PI3K inhibitor.

As used herein, the term "cytotoxic therapy" refers to therapies that induce cellular damage including but not limited to radiation, chemotherapy, photodynamic therapy, radiofrequency ablation, anti-angiogenic therapy, and combinations thereof. A cytotoxic therapeutic may induce DNA damage when applied to a cell.

As used herein, "delaying progression of a disease" or "decreasing the rate of progression of a disease" means to defer, hinder, slow, retard, stabilize, and/or postpone development of the disease (such as a cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

The term "detection" includes any means of detecting, including direct and indirect detection.

The term "drug" as used herein refers to any substance having biological or detectable activity in vivo. The term drug is meant to encompass cytotoxic agents, cytostatic agents, anti-angiogenic agents, debulking agents, chemotherapeutic agents, radiotherapeutic agents, targeted anti-cancer agents, biological response modifiers, cancer vaccines, cytokines, hormone therapies, anti-metastatic agents and immunotherapeutic agents.

The term "drug resistance" refers to the condition when a disease does not respond to the treatment of a drug or drugs. Drug resistance can be either intrinsic (or primary resistance), which means the disease has never been responsive to the drug or drugs, or it can be acquired, which means the disease ceases responding to a drug or drugs that the disease had previously responded to (secondary resistance). In certain embodiments, drug resistance is intrinsic. In certain embodiments, the drug resistance is acquired.

An "effective amount" is at least the minimum amount required to effect a measurable improvement or prevention of a particular disorder. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the cancer or tumor. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved. The effective amount of a treatment can be measured by various endpoints commonly used in evaluating cancer treatments, including, but not limited to: extending survival (including overall survival (OS) and progression free survival (PFS)); resulting in an objective response (including a complete response (CR) or a partial response (PR)); tumor regression, tumor weight or size shrinkage, longer time to disease progression, increased duration of survival, longer PFS, improved OS rate, increased duration of response, and improved quality of life and/or improving signs or symptoms of cancer. As used herein, the term "progressive disease" (PD) refers to least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm The appearance of one or more new lesions is also considered progression. As used herein, the term "partial response" (PR) refers to at least a 30% decrease in the sum of diameters of target lesions, taking as reference the baseline sum diameters. As used herein, the term "complete response" (CR) refers to the disappearance of all non-nodal target lesions with the short axes of any target lymph nodes reduced to <10 mm. As used herein, the term "stable disease" (SD) refers to neither sufficient shrinkage for PR nor sufficient increase to qualify for PD, taking as reference the smallest sum of diameters while on study.

The term "epitope" refers to that portion of a molecule capable of being recognized by and bound by an antibody at one or more of the antibody's antigen-binding portions. Epitopes often consist of a surface grouping of molecules such as amino acids or sugar side chains and have specific three-dimensional structural characteristics as well as specific charge characteristics. In some embodiments, the epitope can be a protein epitope. Protein epitopes can be linear or conformational. In a linear epitope, all of the points of interaction between the protein and the interacting molecule (such as an antibody) occur linearly along the primary amino acid sequence of the protein. A "non-linear epitope" or "conformational epitope" comprises non-contiguous polypeptides (or amino acids) within the antigenic protein to which an antibody specific to the epitope binds. Once a desired epitope on an antigen is determined, it is possible to generate antibodies to that epitope, e.g., using the techniques described in the present specification. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to a target antigen (e.g., EOMES-641K-Ac, EOMES-641K-Me, EOMES-373K-Me etc.), e.g., the antibodies compete for binding to the antigen.

The term "expression" with respect to a gene sequence refers to transcription of the gene to produce a RNA transcript (e.g., mRNA, antisense RNA, siRNA, shRNA, miRNA, etc.) and, as appropriate, translation of a resulting mRNA transcript to a protein. Thus, as will be clear from the context, expression of a coding sequence results from transcription and translation of the coding sequence. Conversely, expression of a non-coding sequence results from the transcription of the non-coding sequence.

As used herein, the term "increase" or "increased" with reference to a biomarker or biomarker complex level refers to a statistically significant and measurable increase in the biomarker or biomarker complex level compared to the level of another biomarker or biomarker complex or to a control level. The increase is preferably an increase of at least about 10%, or an increase of at least about 20%, or an increase of at least about 30%, or an increase of at least about 40%, or an increase of at least about 50%.

As used herein, the term "higher" with reference to a biomarker or biomarker complex measurement refers to a statistically significant and measurable difference in the level of a biomarker or biomarker complex measurement compared to the level of another biomarker or biomarker complex or to a control level where the biomarker or biomarker complex measurement is greater than the level of the other biomarker or biomarker complex or the control level. The difference is preferably at least about 10%, or at least about 20%, or of at least about 30%, or of at least about 40%, or at least about 50%.

As used herein, the term "reduce" or "reduced" with reference to a biomarker or biomarker complex level refers to a statistically significant and measurable reduction in the biomarker or biomarker complex level compared to the level of another biomarker or biomarker complex or to a control level. The reduction is preferably a reduction of at least about 10%, or a reduction of at least about 20%, or a reduction of at least about 30%, or a reduction of at least about 40%, or a reduction of at least about 50%.

As used herein, the term "lower" with reference to a biomarker or biomarker complex measurement refers to a statistically significant and measurable difference in the level of a biomarker or biomarker complex measurement compared to the level of another biomarker or biomarker complex or to a control level where the biomarker or biomarker complex measurement is less than the level of the other biomarker or biomarker complex or the control level. The difference is preferably at least about 10%, or at least about 20%, or of at least about 30%, or of at least about 40%, or at least about 50%.

The terms "level of expression" or "expression level" in general are used interchangeably and generally refer to the amount of a biomarker in a sample. "Expression" generally refers to the process by which information (e.g., gene-encoded and/or epigenetic) is converted into the structures present and operating in the cell. Therefore, as used herein, "expression" may refer to transcription into a polynucleotide, translation into a polypeptide, or even polynucleotide and/or polypeptide modifications (e.g., posttranslational modification of a polypeptide). Fragments of the transcribed polynucleotide, the translated polypeptide, or polynucleotide and/or polypeptide modifications (e.g., post-translational modification of a polypeptide) shall also be regarded as expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (e.g., transfer and ribosomal RNAs). Thus, "elevated expression", "elevated expression levels", or "elevated levels" refers to an increased expression or increased levels of a biomarker in a cell or individual relative to a control, such as a cell or cells that are responding or not responding to a therapy, or an individual or individuals who are responding or not responding to a therapy, or an internal control (e.g., housekeeping biomarker). "Reduced expression", "reduced expression levels", or "reduced levels" refers to a decreased expression or decreased levels of a biomarker in an individual relative to a control, such as a cell or cells that are responding or not responding to a therapy, or an individual or individuals who are responding or not responding to a therapy, an internal control (e.g., housekeeping biomarker). In some embodiments, reduced expression is little or no expression. In specific embodiments, an elevated level of EOMES-641K-Ac refers to a level that correlates with a largely nuclear localization of EOMES or a localization that is higher in the nucleus than in the cytoplasm. An elevated level of EOMES-641K-Ac also can correlate with resistance to therapy. In other embodiments, an elevated level of EOMES-641K-Me refers to a level that correlates with a largely cytoplasmic localization of EOMES or a localization that is higher in the cytoplasm and/or cell membrane than in the nucleus. An elevated level of EOMES-641K-Me also can correlate with responsiveness to therapy.

The term "housekeeping biomarker" refers to a biomarker or group of biomarkers (e.g., polynucleotides and/or polypeptides) which are typically similarly present in all cell types. In some embodiments, the housekeeping biomarker is a "housekeeping gene." A "housekeeping gene" refers herein to a gene or group of genes which encode proteins whose activities are essential for the maintenance of cell function and which are typically similarly present in all cell types.

A "growth inhibitory agent" when used herein refers to a compound or composition which inhibits growth of a cell either in vitro or in vivo. In one embodiment, growth inhibitory agent is growth inhibitory antibody that prevents or reduces proliferation of a cell expressing an antigen to which the antibody binds. In another embodiment, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERER, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "immune checkpoint molecule" includes both receptors and ligands that function as an immune checkpoint. Immune checkpoints represent immune escape mechanisms to prevent the immune system from attacking its own body. Immune checkpoint receptors are present on T-cells, and interact with immune checkpoint ligands expressed on antigen-presenting cells, including cancer cells. T-cells recognize an antigen presented on the MHC molecule and are activated to generate an immune reaction, whereas an interaction between immune checkpoint receptor and ligand that occurs in parallel with the above controls the activation of T-cells. Immune checkpoint receptors include co-stimulatory receptors and inhibitory receptors, and the T-cell activation and the immune reaction are controlled by a balance between both receptors. Illustrative immune checkpoint molecules that may be targeted for blocking or inhibition include, but are not limited to, CTLA-4, 4-1BB (CD137), 4-1BBL (CD137L), PD-L1, PD-L2, PD-1, B7-H3, B7-H4, BTLA, HVEM, TIM3, GAL9, LAG3, TIM3, B7H3, B7H4, VISTA, KIR, 2B4 (belongs to the CD2 family of molecules and is expressed on all NK, γδ, and memory $CD8^{+}$(αβ) T-cells), CD160 (also referred to as BY55) and CGEN-15049.

As used herein, the term "immune checkpoint inhibitor" or "checkpoint inhibitor" refers to any agent, molecule, compound, chemical, protein, polypeptide, macromolecule, etc. that totally or partially reduce, inhibit, interfere with or modulate one or more immune checkpoint molecules. Such inhibitors may include small molecule inhibitors or may include antigen-binding molecules that bind to and block or inhibit immune checkpoint receptors or antibodies that bind to and block or inhibit immune checkpoint receptor ligands. Illustrative immune checkpoint inhibitors include anti-immune checkpoint molecule antagonist antibodies such as, but not limited to, durvalumab (anti-PD-L1 antibody; MEDI4736), pembrolizumab (anti-PD-1 monoclonal antibody), nivolumab (anti-PD-1 antibody), pidilizumab (CT-011; humanized anti-PD-1 monoclonal antibody), AMP224 (recombinant B7-DC-Fc fusion protein), BMS-936559 (anti-PD-L1 antibody), atezolizumab (MPLDL3280A; human Fc-optimized anti-PD-L1 monoclonal antibody), avuelumab (MSB0010718C; human anti-PD-L1 antibody), ipilimumab (anti-CTLA-4 checkpoint inhibitor), tremelimumab (CTLA-4 blocking antibody), and anti-OX40.

The term "immune effector cells" in the context of the present invention relates to cells which exert effector functions during an immune reaction. For example, such cells secrete cytokines and/or chemokines, kill microbes, secrete antibodies, recognize infected or cancerous cells, and optionally eliminate such cells. For example, immune effector cells comprise T-cells (cytotoxic T-cells, helper T-cells, tumor infiltrating T-cells), B-cells, natural killer (NK) cells, lymphokine-activated killer (LAK) cells, neutrophils, macrophages, and dendritic cells.

The term "immune response" refers to any detectable response to a particular substance (such as an antigen or immunogen) by the immune system of a host mammal, such as innate immune responses (e.g., activation of Toll receptor signaling cascade), cell-mediated immune responses (e.g., responses mediated by T-cells, such as antigen-specific T-cells, and non-specific cells of the immune system), and humoral immune responses (e.g., responses mediated by B cells, such as generation and secretion of antibodies into the plasma, lymph, and/or tissue fluids).

The term "immune function" or "function" with respect to a T-cell, and in particular a CD8+ T-cell, refers to the ability of a T-cell to proliferate, be activated, and or be cytolytic. The immune function of a T-cell can be assessed using well known functional assays that measure any one or more of proliferation, activation or cytolysis. In particular examples, the anti-tumor activity of a T-cell is used to assess its immune function. Alternatively, the expression and/or secretion of various effector proteins in the T-cell can be assessed, such as, for example, IFN-γ, TNF-α, IL-2, Ki67, or CD107a. For example, IFN-γ, IL-2, and TNF can be used as biomarkers for $CD8^+$ T-cell activation; CD107a can be used a marker for degranulation; and Ki67 can be used as a biomarker for T-cell proliferation. A functional T cell or population of T cells, and in particular a functional $CD8^+$ T cell or population of $CD8^+$ T cells, is therefore one that can proliferate, be activated and/or be cytolytic at the level expected of T cells from a healthy subject, as assessed using the assays and/or effector proteins/biomarkers described above and herein. Conversely, a dysfunctional T cell or population of T cells, such as a dysfunctional $CD8^+$ T cell or population of $CD8^+$ T cells, has reduced or decreased ability to proliferate, be activated and/or by cytolytic, e.g. has reduced or decreased levels of proliferation, activation and/or cytolysis, as assessed using the assays and/or effector proteins/biomarkers described above and herein (e.g. reduced or decreased by about or at least, 20%, 25%, 30%, 35%, 40%, 45%, 50%, 55%, 60%, 65%, 70%, 75%, 70%, 85%, 90% or 95% compared to a functional T cell or population of T cells).

The term "immunotherapy" refers to any therapy in which one or more components of a human's or animal's immune system is deliberately modulated in order to directly or indirectly achieve some therapeutic benefit, including systemic and/or local effects, and preventative and/or curative effects. Immunotherapy can involve administering one or more immunotherapeutic agents, either alone or in any combination, to a human or animal subject by any route (e.g., orally, intravenously, dermally, by injection, by inhalation, etc.), whether systemically, locally or both. Immunotherapy can involve provoking, increasing, decreasing, halting, preventing, blocking or otherwise modulating the production of cytokines, and/or activating or deactivating cytokines or immune cells, and/or modulating the levels of immune cells, and/or delivering one or more therapeutic or diagnostic substances to a particular location in the body or to a particular type of cell or tissue, and/or destroying particular cells or tissue. Immunotherapy can be used to achieve local effects, systemic effects or a combination of both.

The term "immunotherapeutic agent" as used herein refers to any agent, compound, or biologic that indirectly or directly restores, enhances, stimulates or increases the body's immune response against cancer cells and/or that decreases the side effects of other anticancer therapies. Immunotherapy is thus a therapy that directly or indirectly stimulates or enhances the immune system's responses to cancer cells and/or lessens the side effects that may have been caused by other anti-cancer agents. Immunotherapy is also referred to in the art as immunologic therapy, biological therapy biological response modifier therapy and biotherapy. Examples of common immunotherapeutic agents known in the art include, but are not limited to, cytokines, cancer vaccines, monoclonal antibodies and non-cytokine adjuvants. Alternatively the immunotherapeutic treatment may consist of administering the subject with an amount of immune cells (T cells, NK, cells, dendritic cells, B cells, etc.). Immunotherapeutic agents can be non-specific, i.e., boost the immune system generally so that the human body becomes more effective in fighting the growth and/or spread of cancer cells, or they can be specific, i.e., targeted to the cancer cells themselves. Immunotherapy regimens may combine the use of non-specific and specific immunotherapeutic agents. Non-specific immunotherapeutic agents are substances that stimulate or indirectly improve the immune system. Non-specific immunotherapeutic agents have been used alone as a main therapy for the treatment of cancer, as well as in addition to a main therapy, in which case the non-specific immunotherapeutic agent functions as an adjuvant to enhance the effectiveness of other therapies (e.g., cancer vaccines). Non-specific immunotherapeutic agents can also function in this latter context to reduce the side effects of other therapies, for example, bone marrow suppression induced by certain chemotherapeutic agents. Non-specific immunotherapeutic agents can act on key immune system cells and cause secondary responses, such as increased production of cytokines and immunoglobulins. Alternatively, the agents can themselves comprise cytokines. Non-specific immunotherapeutic agents are generally classified as cytokines or non-cytokine adjuvants. A number of cytokines have found application in the treatment of cancer either as general non-specific immunotherapies designed to boost the immune system, or as adjuvants provided with other therapies. Suitable cytokines include, but are not limited to, interferons, interleukins and colony-stimulating factors. Interferons (IFNs) contemplated by the present invention include the common types of IFNs, IFN-alpha (IFN-α), IFN-beta (IFN-β) and IFN-gamma (IFN-γ). IFNs can act directly on cancer cells, for example, by slowing their growth, promoting their development into cells with more normal behaviour and/or increasing their production of antigens thus making the cancer cells easier for the immune system to recognise and destroy. IFNs can also act indirectly on cancer cells, for example, by slowing down angiogenesis, boosting the immune system and/or stimulating natural killer (NK) cells, T-cells and macrophages. Recombinant IFN-alpha is available commercially as Roferon (Roche Pharmaceuticals) and Intron A (Schering Corporation). Interleukins contemplated by the present invention include IL-2, IL-4, IL-11 and IL-12. Examples of commercially available recombinant interleukins include Proleukin® (IL-2; Chiron Corporation) and Neumega® (IL-12; Wyeth Pharmaceuticals). Zymogenetics, Inc. (Seattle, Wash.) is currently testing a recombinant form of IL-21, which is also contemplated for use in the combinations of the present invention. Colony-stimulating factors (CSFs) contemplated by the present invention include granulocyte colony stimulating factor (G-CSF or filgrastim), granulocyte-macrophage colony stimulating factor (GM-CSF or sargramostim) and erythropoietin (epoetin alfa, darbopoietin). Treatment with one or more growth factors can help to stimulate the generation of new blood cells in subjects undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, Neupogen® (G-CSF; Amgen), Neulasta (pelfilgrastim; Amgen), Leukine (GM-CSF; Berlex), Procrit (erythropoietin; Ortho Biotech), Epogen (erythropoietin; Amgen), Aranesp (erythropoietin). In addition to having specific or non-specific targets, immunotherapeutic agents can be active, i.e., stimulate the body's own immune response including humoral and cellular immune responses, or they can be passive, i.e., comprise immune system components such as antibodies, effector immune cells, antigen-presenting cells etc. that were generated external to the body. In specific embodiments, passive immunotherapy involves the use of one or more monoclonal antibodies that are specific for a particular antigen found on the surface of a cancer cell or immune cell or that are specific for a particular cell growth factor. Monoclonal antibodies may be used in the treatment of cancer in a number of ways, for example, to enhance a subject's immune response to a specific type of cancer, to interfere with the growth of cancer cells by targeting specific cell growth factors, such as those involved in angiogenesis, or by enhancing the delivery of other anticancer agents to cancer cells when linked or conjugated to agents such as chemotherapeutic agents, radioactive particles or toxins. Monoclonal antibodies currently used as cancer immunotherapeutic agents include, but are not limited to, alemtuzumab (LEMTRADA®), bevacizumab (AVASTIN®), cetuximab (ERBITUX®), panitumumab (VECTIBIX®), pertuzumab (OMNITARG®, 2C4), trastuzumab (HERCEPTIN®), tositumomab (Bexxar®), abciximab (REOPRO®), adalimumab (HUMIRA®), apolizumab, aselizumab, atlizumab, bapineuzumab, basiliximab (SIMULECT®), bavituximab, belimumab (BENLYSTA®) briankinumab, canakinumab (ILARIS®), cedelizumab, certolizumab pegol (CIMZIA®), cidfusituzumab, cidtuzumab, cixutumumab, clazakizumab, crenezumab, daclizumab (ZENAPAX®), dalotuzumab, denosumab (PROLIA®, XGEVA®), eculizumab (SOLIRIS®), efalizumab, epratuzumab, erlizumab, felvizumab, fontolizumab, golimumab (SIMPONI®), ipilimumab, imgatuzumab, infliximab (REMICADE®), labetuzumab, lebrikizumab, lexatumumab, lintuzumab, lucatumumab, lulizumab pegol, lumretuzumab, mapatumumab, matuzumab, mepolizumab, mogamulizumab, motavizumab, motovizumab, muronomab, natalizumab (TYSABRI®), necitumumab (PORTRAZZA®), nimotuzumab (THERACIM®), nolovizumab, numavizumab, olokizumab, omalizumab (XOLAIR®), onartuzumab (also known as MetMAb), palivizumab (SYNAGIS®), pascolizumab, pecfusituzumab, pectuzumab, pembrolizumab (KEYTRUDA®), pexelizumab, priliximab, ralvizumab, ranibizumab, (LUCENTIS®), reslivizumab, reslizumab, resyvizumab, robatumumab, rontalizumab, rovelizumab, ruplizmnab, sarilumab, secukinumab, seribantumab, sifalimumab, sibrotuzumab, siltuximab (SYLVANT®) siplizumab, sontuzumab, tadocizumab, talizumab, tefibazumab, tocilizumab (ACTEMRA®), toralizumab, tucusituzumab, umavizmab, urtoxazumab, ustekinumab (STELARA®), vedolizumab (ENTYVIO®), visilizumab, zanolimumab, zalutumumab.

As used herein, "instructional material" includes a publication, a recording, a diagram, or any other medium of expression which can be used to communicate the usefulness of the compositions and methods of the invention. The instructional material of the kit of the invention may, for example, be affixed to a container which contains the therapeutic or diagnostic agents of the invention or be shipped together with a container which contains the therapeutic or diagnostic agents of the invention.

The term "label" when used herein refers to a detectable compound or composition. The label is typically conjugated or fused directly or indirectly to a reagent, such as a polynucleotide probe or an antibody, and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which results in a detectable product.

As used herein, the term "localize" and its grammatical equivalent mean to accumulate in, or be restricted to, a specific or limited space or area, for example a specific cell, tissue, organelle, or intracellular region such as a cellular compartment (e.g., nucleus, cytoplasm, nuclear membrane, cell membrane, etc.).

The term "multiplex-PCR" refers to a single PCR reaction carried out on nucleic acid obtained from a single source (e.g., an individual) using more than one primer set for the purpose of amplifying two or more DNA sequences in a single reaction.

The terms "patient", "subject", "host" or "individual" used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates (e.g., humans, monkeys and apes, and includes species of monkeys such from the genus *Macaca* (e.g., cynomologus monkeys such as *Macaca fascicularis*, and/or rhesus monkeys (*Macaca* mulatta)) and baboon (Papio *ursinus*), as well as marmosets (species from the genus Callithrix), squirrel monkeys (species from the genus Saimiri) and tamarins (species from the genus Saguinus), as well as species of apes such as chimpanzees (Pan troglodytes)), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as *canaries*, budgerigars etc.), marine mammals (e.g., dolphins, whales), reptiles (snakes, frogs, lizards etc.), and fish. A preferred subject is a human with cancer.

The term "pharmaceutical composition" or "pharmaceutical formulation" refers to a preparation which is in such form as to permit the biological activity of the active ingredient(s) to be effective, and which contains no additional components which are unacceptably toxic to a subject to which the composition or formulation would be administered. Such formulations are sterile. "Pharmaceutically acceptable" excipients (vehicles, additives) are those which can reasonably be administered to a subject mammal to provide an effective dose of the active ingredient employed.

The term "predictive" and grammatical forms thereof, generally refer to a biomarker or biomarker signature that provides a means of identifying, directly or indirectly, a likelihood of a patient responding to a therapy or obtaining a clinical outcome in response to therapy.

The term "prognostic" and grammatical forms thereof, generally refer to an agent or method that provides information regarding the likely progression or severity of a disease or condition in an individual. In some embodiments, prognosis also refers to the ability to demonstrate a positive or negative response to therapy or other treatment regimens, for the disease or condition in the subject. In some embodiments, prognosis refers to the ability to predict the presence or diminishment of disease/condition associated symptoms. A prognostic agent or method may comprise classifying a subject or sample obtained from a subject into one of multiple categories, wherein the categories correlate with different likelihoods that a subject will experience a particular outcome. For example, categories can be low risk and high risk, wherein subjects in the low risk category have a lower likelihood of experiencing a poor outcome (e.g., within a given time period such as 5 years or 10 years) than do subjects in the high risk category. A poor outcome could be, for example, disease progression, disease recurrence, or death attributable to the disease.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

As used herein, a cancer patient (or subject with cancer) who has been treated with a therapy is considered to "respond", have a "response", have "a positive response" or be "responsive" to the therapy if the subject shows evidence of an anti-cancer effect according to an art-accepted set of objective criteria or reasonable modification thereof, including a clinically significant benefit, such as the prevention, or reduction of severity, of symptoms, or a slowing of the progression of the cancer. It will be understood that the aforementioned terms may also be used in regard to the cancer. A variety of different objective criteria for assessing the effect of anti-cancer treatments on cancers are known in the art. The World Health Organization (WHO) criteria (Miller, A B, et al., *Cancer* 1981; 47 (1): 207-14) and modified versions thereof, the Response Evaluation Criteria in Solid Tumors (RECIST) (Therasse P, et al., *J Natl Cancer Inst* 2000; 92:205-16), and revised version thereof (Eisenhauer E A, New response evaluation criteria in solid tumors:

revised RECIST guideline (version 1.1). *Eur J Cancer* 2009; 45 (2): 228-47) are sets of objective criteria, based on imaging measurements of the size and number of tumor lesions and detection of new lesions, e.g., from computed tomography (CT), magnetic resonance imaging (MRI), or conventional radiographs. Dimensions of selected lesions (referred to as target lesions) are used to calculate the change in tumor burden between images from different time points. The calculated response is then categorized as complete response (CR), partial response (PR), stable disease (SD), or progressive disease (PD). CR is complete disappearance of tumor (−100%), and PD is an increase of about 20%-25% or greater (depending on the particular criteria) and/or the appearance of new lesions. PR is a significant reduction (of at least about 30%) in size of tumor lesions (without emergence of new lesions) but less than a complete response. SD is in between PR and PD. (See Tables 1 and 2 for details.) These criteria are widely used as a primary endpoint in Phase II trials evaluating the efficacy of anti-cancer agents, e.g., as a surrogate for overall survival. However, anatomic imaging alone using WHO, RECIST, and RECIST 1.1 criteria were designed to detect early effects of cytotoxic agents and have certain limitations, particularly in assessing the activity of newer cancer therapies that stabilize disease. Clinical response patterns in patients treated with immunotherapeutic anti-cancer agents or molecularly targeted anti-cancer agents may extend beyond those of cytotoxic agents and can manifest after an initial increase in tumor burden or the appearance of new lesions. For example, meaningful tumor responses to immune checkpoint inhibitor may occur after a delay, in some cases following WHO- or RECIST-defined PD. Criteria designated immune-related response criteria (irRC) were defined in an attempt to capture additional favorable response patterns observed with immune therapies (Wolchok, J D, et al. (2009) Guidelines for the evaluation of immune therapy activity in solid tumors: immune-related response criteria. *Clin. Care Res.* 15, 7412-7420.). Four patterns associated with favorable survival were identified, i.e., decreased baseline lesions without new lesions; durable stable disease; initial increase in total tumor burden but eventual response; and a reduction in total tumor burden during or after the appearance of new lesion(s), of which the latter two are distinct from the response patterns considered favorable according to WHO or RECIST criteria. The irRC include criteria for complete response (irCR), partial response (irPR), stable disease (irSD), and progressive disease (irPD). Among other things, the irRC incorporates measurable new lesions into "total tumor burden" and compares this variable to baseline measurements rather than assuming that new lesions necessarily represent progressive disease. In summary, according to the immune-related response criteria, irCR is complete disappearance of all lesions whether measurable or not, and no new lesions; irPR is a decrease in tumor burden ≥50% relative to baseline; irSD is disease not meeting criteria for irCR or irPR, in absence of it progressive disease (irPD); irPD is an increase in tumor burden.gtoreq.25% relative to nadir (the minimum recorded tumor burden) (Wolchok, supra). irCR, irPR and irPD require confirmation by a repeat, consecutive assessment at least 4 weeks from the date of first documentation. irCR, irPR, and irSD include all patients with CR, PR, or SD by WHO criteria as well as those patients that shift to these irRC categories from WHO PD. However, some patients who would be classified as having PD according to WHO or RECIST criteria are instead classified as having PR or SD according to the irRC, identifying them as likely to have favorable survival. The irRC are applicable to immune checkpoint inhibitors and other immunotherapeutic agents. One of ordinary skill in the art will appreciate that additional response criteria are known in the art, which take into consideration various factors such as changes in the degree of tumor arterial enhancement and/or tumor density as indicators of tumor viable tissue, with decreased arterial enhancement and decreased tumor density being indicators of reduced viable tumor tissue (e.g., due to tumor necrosis). For example, modified RECIST criteria (mRECIST) take into consideration changes in the degree of tumor arterial enhancement (Lencioni R and Llovet J M. *Semin Liver Dis* 30:52-60, 2010). Choi criteria and modified Choi criteria take into consideration decrease in tumor density on CT. Choi H, et al., *J Clin Oncol* 25:1753-1759, 2007; Nathan P D, et al., *Cancer Biol Ther* 9:15-19, 2010; Smith A D, et al., *Am J Roentgenol* 194:157-165, 2010. Such criteria may be particularly useful in certain cancer types and/or with certain classes of therapeutic agents. For example, changes in tumor size can be minimal in tumors such as lymphomas, sarcoma, hepatomas, mesothelioma, and gastrointestinal stromal tumor despite effective treatment. CT tumor density, contrast enhancement, or MRI characteristics appear more informative than size. In certain embodiments functional imaging, e.g., using positron emission tomography (PET) may be used. For example, PET response criteria in solid tumors (PERCIST) may be used, in which the treatment response is evaluated by metabolic changes assessed with (18) F-FDG PET imaging, with decreased uptake of the tracer being indicative of (Wahl R L, et al., *J Nucl Med* 2009; 50, Suppl 1: 122S-50S). It will also be understood that response criteria developed for various specific cancer types such as melanoma, breast cancer and lung cancer, are known in the art. By contrast, a cancer patient who has been treated with a therapy is considered "not to respond", "to lack a response", to have "a negative response" or be "non-responsive" to the therapy if the therapy provides no clinically significant benefit, such as the prevention, or reduction of severity, of symptoms, or increases the rate of progression of the cancer.

For purposes of the present disclosure, a cancer patient treated with an immunotherapy (e.g., an immune checkpoint inhibitor) as monotherapy or in combination with one or more other active agents (e.g., a complement inhibitor, an additional anti-cancer agent, or both) is considered to "respond", have a "response", or be "responsive" to the treatment if the patient has a complete response, partial response, or stable disease according at least to the immune-related response criteria. (The cancer patient may also respond according to RECIST, RECIST 1.1, WHO, and/or other criteria such as those mentioned above.) Likewise, the cancer in such cases is said to “respond”, be “responsive”, or be “sensitive” to the treatment. The cancer patient is considered to “not respond”, not have a “response”, or to be “nonresponsive” to the treatment if the patient has progressive disease according to the immune-related response criteria. (The cancer patient may also not respond according to RECIST, RECIST 1.1, WHO, and/or other criteria such as those mentioned above). Likewise, the cancer in such cases said to “not respond”, or to be “nonresponsive”, “insensitive” or “resistant” to the treatment. (A cancer is also considered to have become resistant to treatment if it initially responds but the patient subsequently exhibits progressive disease in the presence of treatment.) Thus, for example, for methods and products described herein that relate to response to treatment for cancer (e.g., methods of predicting likelihood of response, methods of classifying patients according to predicted response, methods of increasing the likelihood of response) a response is defined as irCR, irPR, or irSD, and lack of response is defined as irPD unless otherwise specified. In certain embodiments any useful response criteria may be specified. The response criteria may have been shown to correlate with a benefit such as increased overall survival or other clinically significant benefit. It will be appreciated that refinements or revisions of existing response criteria that, e.g., encompass additional favorable patterns of clinical activity (e.g., correlating with increased overall survival) applicable to immune checkpoint inhibitors or are otherwise useful may be developed in the future. In certain embodiments any such response criteria may be specified for use in methods described herein.

The term “sample” as used herein includes any biological specimen that may be extracted, untreated, treated, diluted or concentrated from a subject. A sample includes within its scope a collection of similar fluids, cells, or tissues (e.g., surgically resected tumor tissue, biopsies, including fine needle aspiration), isolated from a subject, as well as fluids, cells, or tissues present within a subject. In some embodiments the sample is a biological fluid. Biological fluids are typically liquids at physiological temperatures and may include naturally occurring fluids present in, withdrawn from, expressed or otherwise extracted from a subject or biological source. Certain biological fluids derive from particular tissues, organs or localized regions and certain other biological fluids may be more globally or systemically situated in a subject or biological source. Examples of biological fluids include blood, serum and serosal fluids, plasma, lymph, urine, saliva, cystic fluid, tear drops, feces, sputum, mucosal secretions of the secretory tissues and organs, vaginal secretions, ascites fluids such as those associated with non-solid tumors, fluids of the pleural, pericardial, peritoneal, abdominal and other body cavities, fluids collected by bronchial lavage and the like. Biological fluids may also include liquid solutions contacted with a subject or biological source, for example, cell and organ culture medium including cell or organ conditioned medium, lavage fluids and the like. The term “sample” as used herein encompasses materials removed from a subject or materials present in a subject.

A “reference sample”, “reference cell”, “reference tissue”, “reference level” “control sample”, “control cell”, “control tissue” or “control level”, as used herein, refers to a sample, cell, tissue, standard, or level that is used for comparison purposes. In one embodiment, a reference sample, reference cell, reference tissue, control sample, control cell, or control tissue is obtained from a healthy and/or non-diseased part of the body (e.g., tissue or cells) of the same subject or individual, but at different time-points, e.g. before and after therapy. In another embodiment, a reference sample, reference cell, reference tissue, control sample, control cell, or control tissue is obtained from a healthy individual who is not the subject or individual being assessed. In particular examples, a reference sample, reference cell, reference tissue, control sample, control cell, or control tissue is or comprises a functional T-cell, a dysfunctional T-cell (e.g. an exhausted T-cell), T-cells from a subject that is responsive or sensitive to therapy or T-cells from a subject that is non-responsive or resistant to therapy. In particular embodiments, the T-cell are $CD8^{+}$ T-cells, Various methodologies of the instant invention include a step that involves comparing a value, level, feature, characteristic, property, etc. to a “suitable control,” referred to interchangeably herein as an “appropriate control,” a “control sample” or a “reference.” A “suitable control”, “appropriate control”, “control sample” or a “reference” is any control or standard familiar to one of ordinary skill in the art useful for comparison purposes. In some embodiments, a “suitable control” or “appropriate control” is a value, level, feature, characteristic, property, etc., determined in a cell, tissue, or patient, e.g., a control cell, cell population, tissue, or patient, exhibiting, for example, a particular biomarker profile. A “suitable control” can be a pattern of levels/ratios of one or more biomarkers of the present invention that correlates to a particular biomarker profile, to which a cell sample can be compared. The cell sample can also be compared to a negative control. Such reference levels may also be tailored to specific techniques that are used to measure levels of biomarkers in biological samples (e.g., LC-MS, GC-MS, ELISA, PCR, etc.), where the levels of biomarkers may differ based on the specific technique that is used. Suitable controls may include, for example, functional T-cells, dysfunctional T cells (e.g. exhausted T cells), T-cells from a subject that is responsive or sensitive to cancer therapy, and T-cells from a subject that is non-responsive or resistant to cancer therapy.

As used herein, the terms “stratifying” and “classifying” are used interchangeably herein to refer to sorting of subjects into different strata or classes based on the features of a particular physiological or pathophysiological state or condition. For example, stratifying a population of subjects according to whether they are likely to respond to a therapy (e.g., chemotherapy or immunotherapy) involves assigning the subjects based on levels of response to therapy biomarkers including EOMES-641K-Ac, EOMES-641K-Me and EOMES-373K-Me, in T-cells optionally in combination with one or more other biomarkers (e.g., IFN-$\gamma$, TNF-$\alpha$, IL-2, Ki67, PD-1 or CD107a).

As used herein, the term “treatment” refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully “treated” if one or more symptoms associated with a cancer are mitigated or eliminated, including, but are not limited to, reducing the proliferation of (or destroying) cancerous cells, reducing pathogen infection, decreasing symptoms resulting from the disease, increasing the quality of life of those suffering from the disease, decreasing the dose of other medications required to treat the disease, and/or prolonging survival of individuals. The phrase “treatment with a therapy”, “treating with a therapy”, “treatment with an agent”, “treating with an agent” and the like refers to the administration of an effective amount of a therapy or agent, including a cancer therapy or agent, (e.g., a cytotoxic agent or an immunotherapeutic agent) to a patient, or the concurrent administration of two or more therapies or agents, including cancer therapies or agents, (e.g., two or more agents selected from cytotoxic agents and immunotherapeutic agents) in effective amounts to a patient.

As used herein, “treatment outcome” refers to predicting the response of a cancer patient to a selected therapy or treatment, including the likelihood that a patient will experience a positive or negative outcome with a particular treatment. As used herein, “indicative of a positive treatment outcome” or the like refers to an increased likelihood that the patient will experience beneficial results from the selected treatment (e.g., complete or partial response, complete or partial remission, reduced tumor size, stable disease, etc.). By contrast, “indicative of a negative treatment outcome” or the like is intended to mean an increased likelihood that the patient will not benefit from the selected treatment with respect to the progression of the underlying cancer (e.g., progressive disease, disease recurrence, increased tumor size, etc.).

“Tumor,” as used herein, refers to all neoplastic cell growth and proliferation, whether malignant or benign, and all pre-cancerous and cancerous cells and tissues. The terms “cancer”, “cancerous”, “cell proliferative disorder”, “proliferative disorder” “hyperproliferative disorder” and “tumor” are not mutually exclusive as referred to herein.

As used herein, underscoring or italicizing the name of a gene shall indicate the gene, in contrast to its protein product, which is indicated by the name of the gene in the absence of any underscoring or italicizing. For example, “EOMES” shall mean the EOMES gene, whereas “EOMES” shall indicate the protein product or products generated from transcription and translation and/or alternative splicing of the EOMES gene.

Each embodiment described herein is to be applied mutatis mutandis to each and every embodiment unless specifically stated otherwise.

2. Methods of Detection, Diagnosis and Prognosis

EOMES is a transcription factor linked to T-cell exhaustion and dysfunction. The present invention discloses that different post-translational modifications of a lysine at position 641 of the EOMES polypeptide sequence, which is contained within the NLS of EOMES, or a lysine at position 373 of the EOMES polypeptide, which is contained in the DNA binding domain of EOMES, affect localization of EOMES to the nucleus or to the cytoplasm and likely also affect protein:protein or protein: DNA interactions. Moreover, EOMES polypeptides with different post-translational modifications of these lysines are associated with either functional or dysfunctional T-cells, and can be used to predict responsiveness to cancer therapy.

A representative EOMES polypeptide comprises the following amino acid sequence:

[SEQ ID NO: 1]

MQLGEQLLVSSVNLPGAHFYPLESARGGSGGSAGHLPSAAPSPQKLDLDK

ASKKFSGSLSCEAVSGEPAAASAGAPAAMLSDTDAGDAFASAAAVAKPGP

-continued

PDGRKGSPCGEEELPSAAAAAAAAAAAAAATARYSMDSLSSERYYLQSPG

PQGSELAAPCSLFPYQAAAGAPHGPVYPAPNGARYPYGSMLPPGGFPAAV

CPPGRAQFGPGAGAGSGAGGSSGGGGGPGTYQYSQGAPLYGPYPGAAAAG

SCGGLGGLGVPGSGFRAHVYLCNRPLWLKFHRHQTEMIITKQGRRMFPFL

SFNINGLNPTAHYNVFVEVVLADPNHWRFQGGKWVTCGKADNNMQGNKMY

VHPESPNTGSHWMRQEISFGKLKLTNNKGANNNNTQMIVLQSLHKYQPRL

HIVEVTEDGVEDLNEPSKTQTFTFSETQFIAVTAYQNTDITQLKIDHNPF

AKGFRDNYDSSHQIVPGGRYGVQSFFPEPFVNTLPQARYYNGERTVPQTN

GLLSPQQSEEVANPPQRWLVTPVQQPGTNKLDISSYESEYTSSTLLPYGI

KSLPLQTSHALGYYPDPTFPAMAGWGGRGSYQRKMAAGLPWTSRTSPTVF

SEDQLSKEKVKEEIGSSWIETPPSIKSLDSNDSGVYTSACKRRRLSPSNS

SNENSPSIKCEDINAEEYSKDTSKGMGGYYAFYTTP, wherein the lysines at position 373 (i.e., 373K) and position 641 (i.e. 641K) are highlighted in bold typeface.

The present inventors have found that acetylation of the lysine at position 641 (i.e., EOMES-641K-Ac) largely localizes EOMES to the nucleus of a T-cell (e.g. a $CD8^+$ T-cell). Moreover, expression of EOMES-641K-Ac was associated with dysfunctional T-cells, having an exhausted, senescent T-cell signature (e.g. low or reduced expression of Ki67, TNF-α, and/or IFN-γ). Consistent with this finding was that expression of EOMES-641K-Ac was associated with resistance or non-responsiveness to cancer therapy.

The present inventors also found that methylation of the lysine at position 641 of EOMES (i.e., EOMES-641K-Me), or methylation of the lysine at position 373 of EOMES (i.e., EOMES-373K-Me), including dimethylation (Me2), was associated with a functional T-cell phenotype and responsiveness to cancer therapy. These methylated forms of EOMES tended to localize more to the cytoplasm rather than nucleus, although some nuclear expression was also observed.

Thus, in accordance with the present invention, EOMES-641K-Ac, EOMES-641K-Me, and/or EOMES-373K-Me can be employed as biomarkers for assessing the function of T-cells, predicting the likelihood of response of a subject to a cancer therapy (e.g., chemotherapy and/or immunotherapy), including likelihood of resistance or sensitivity to therapy, stratifying cancer patients as likely responders or non-responders to a therapy, managing treatment of cancer patients with a therapy, and predicting treatment outcomes for cancer patients treated with a therapy.

T-cells for the practice of the present invention can be obtained from any suitable T-cell containing patient samples, illustrative examples of which include liquid biopsies, tumor biopsies, primary cell cultures or cell lines derived from T-cells, as well as preserved tumor samples, such as formalin-fixed, paraffin-embedded tumor samples or frozen tumor samples. In some embodiments, the sample is obtained prior to treatment with a therapy. In other embodiments, the sample is obtained after treatment with a therapy. In some embodiments, the sample comprises a tissue sample, which can be formalin fixed and paraffin embedded, archival, fresh or frozen. In some embodiments, the sample is whole blood. In particular embodiments, the T-cell is a $CD8^+$ T-cell.

Presence and/or levels/amount of a biomarker (e.g., any one or more of EOMES-641K-Ac, EOMES-641K-Me and EOMES-373K-Me, and optionally one or more other biomarkers, such as a biomarker of T-cell function, such as, for example, IFN-γ, TNF-α, IL-2, Ki67, PD-1 or CD107a) can be determined qualitatively and/or quantitatively based on any suitable criterion known in the art, including but not limited to proteins and protein fragments. In certain embodiments, presence and/or expression levels/amount of a biomarker in a first sample is increased or elevated as compared to presence/absence and/or expression levels/amount in a second sample (e.g., before treatment with a therapy). In certain embodiments, presence/absence and/or levels/amount of a biomarker in a first sample is decreased or reduced as compared to presence and/or levels/amount in a second sample. In certain embodiments, the second sample is a reference sample, reference cell, reference tissue, control sample, control cell, or control tissue. Additional disclosures for determining presence/absence and/or levels/amount of a gene are described herein.

In some embodiments of any of the methods, an elevated level refers to an overall increase of about any of 10%, 20%, 30%, 40%, 50%, 60%, 70%, 80%, 90%, 95%, 96%, 97%, 98%, 99% or greater, in the level of biomarker (e.g., protein or nucleic acid), detected by standard art known methods such as those described herein, as compared to a reference sample, reference cell, reference tissue, control sample, control cell, or control tissue. In certain embodiments, an elevated level refers to the increase in level/amount of a biomarker in the sample wherein the increase is at least about any of 1.5x, 1.75x, 2x, 3x, 4x, 5x, 6x, 7x, 8x, 9x, 10x, 25x, 50x, 75x, or 100× the level/amount of the respective biomarker in a reference sample, reference cell, reference tissue, control sample, control cell, or control tissue. In some embodiments, an elevated level refers to an overall increase of greater than about 1.5-fold, about 1.75-fold, about-2 fold, about 2.25-fold, about 2.5-fold, about 2.75-fold, about 3.0-fold, or about 3.25-fold as compared to a reference sample, reference cell, reference tissue, control sample, control cell, control tissue, or internal control (e.g., housekeeping gene).

In some embodiments of any of the methods, a reduced level refers to an overall reduction of about any of 10%, 20%, 30%, 40%, 50%, 60%, 70%, 80%, 90%, 95%, 96%, 97%, 98%, 99% or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In certain embodiments, reduced level refers to a decrease in level/amount of a biomarker in the sample wherein the decrease is at least about any of 0.9×, 0.8×, 0.7×, 0.6×, 0.5×, 0.4×, 0.3×, 0.2×, 0.1×, 0.05×, or 0.01× the level/amount of the respective biomarker in a reference sample, reference cell, reference tissue, control sample, control cell, or control tissue.

Presence and/or level/amount of various biomarkers in a sample can be analyzed by a number of methodologies, many of which are known in the art and understood by the skilled artisan, including, but not limited to, immunohistochemistry ("IHC"), Western blot analysis, immunoprecipitation, molecular binding assays, ELISA, ELIFA, fluorescence activated cell sorting ("FACS"), MassARRAY, proteomics, quantitative blood based assays (as for example Serum ELISA), biochemical enzymatic activity assays, in situ hybridization, Southern analysis, Northern analysis, whole genome sequencing, polymerase chain reaction ("PCR") including quantitative real time PCR ("qRT-PCR") and other amplification type detection methods, such as, for example, branched DNA, SISBA, TMA and the like), RNA-Seq, FISH, microarray analysis, gene expression profiling, and/or serial analysis of gene expression ("SAGE"), as well as any one of the wide variety of assays that can be performed by protein, gene, and/or tissue array analysis. Typical protocols for evaluating the status of genes and gene products are found, for example in Ausubel et al., eds., 1995, Current Protocols In Molecular Biology, Units 2 (Northern Blotting), 4 (Southern Blotting), 15 (Immunoblotting) and 18 (PCR Analysis). Multiplexed immunoassays such as those available from Rules Based Medicine or Meso Scale Discovery ("MSD") may also be used.

In some embodiments, presence and/or level/amount of a biomarker, particularly for biomarkers not characterized by post-translational modification (e.g. IFN-γ, TNF-α, IL-2, Ki67, PD-1 or CD107a), is determined using a method comprising: (a) performing gene expression profiling, PCR (such as RT-PCR or qRT-PCR), RNA-seq, microarray analysis, SAGE, MassARRAY technique, or FISH on a sample; and b) determining presence and/or expression level/amount of a biomarker in the sample. In some embodiments, the microarray method comprises the use of a microarray chip having one or more nucleic acid molecules that can hybridize under stringent conditions to a nucleic acid molecule encoding a gene mentioned above or having one or more polypeptides (such as peptides or antibodies) that can bind to one or more of the proteins encoded by the genes mentioned above. In one embodiment, the PCR method is qRT-PCR. In one embodiment, the PCR method is multiplex-PCR. In some embodiments, gene expression is measured by microarray. In some embodiments, gene expression is measured by qRT-PCR. In some embodiments, expression is measured by multiplex-PCR.

Methods for the evaluation of mRNAs in cells are well known and include, for example, hybridization assays using complementary DNA probes (such as in situ hybridization using labeled riboprobes specific for the one or more genes, Northern blot and related techniques) and various nucleic acid amplification assays (such as RT-PCR using complementary primers specific for one or more of the genes, and other amplification type detection methods, such as, for example, branched DNA, SISBA, TMA and the like).

Samples from mammals can be conveniently assayed for mRNAs using Northern, dot blot or PCR analysis. In addition, such methods can include one or more steps that allow one to determine the levels of target mRNA in a biological sample (e.g., by simultaneously examining the levels a comparative control mRNA sequence of a "housekeeping" gene such as an actin family member). Optionally, the sequence of the amplified target cDNA can be determined.

Optional methods include protocols which examine or detect mRNAs, such as target mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes whose expression correlates with increased or reduced clinical benefit of a therapy may be arrayed on a solid support. Hybridization of a labeled probe with a particular array member indicates that the sample from which the probe was derived expresses that gene.

In preferred embodiments, presence and/or level/amount is measured by observing protein levels. In certain embodiments, the method comprises contacting the biological sample (such as a sample from a cancer patient) with an antigen-binding molecule (e.g. an antibody) specific for a response to therapy biomarker (e.g., EOMES-641K-Ac, EOMES-641K-Me and/or EOMES-373K-Me) under conditions permissive for binding of the biomarker(s), and detecting whether a complex is formed between the antigen-binding molecule or molecules and the biomarker(s). Such method may be an in vitro or in vivo method. In some embodiments, one or more anti-biomarker antigen-binding molecules are used to select subjects eligible for a therapy e.g., an immunotherapy.

In certain embodiments, the presence and/or expression level/amount of biomarker proteins in a sample is examined using immunohistochemistry (IHC) or immunofluoresence microscopy (IF) protocols. In some embodiments, the level of a response to therapy biomarker (e.g., EOMES-641K-Ac, EOMES-641K-Me and/or EOMES-373K-Me) in a sample from an individual is an elevated level and, in further embodiments, is determined using IHC or IF. In one embodiment, the level of biomarker is determined using a method comprising: (a) performing IHC or IF analysis of a sample (such as a sample from a cancer patient) with an antigen-binding molecule; and b) determining the level of a biomarker in the sample. In some embodiments, IHC or IF staining intensity is determined relative to a reference. In some embodiments, the reference is a reference value. In some embodiments, the reference is a reference sample (e.g., control cell line staining sample or sample from non-cancerous patient or sample from a patient before therapy).

In particular methods, the sample may be contacted with an antigen-binding molecule specific for said biomarker under conditions sufficient for an molecule-biomarker complex to form, and then detecting said complex. The presence of the biomarker may be detected in a number of ways, such as by microscopy (e.g. IF microscopy), Western blotting and ELISA procedures for assaying a wide variety of tissues and samples, including blood. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labeled antibody to a target biomarker.

In certain embodiments, the samples are normalized for both differences in the amount of the biomarker assayed and variability in the quality of the samples used, and variability between assay runs. Such normalization may be accomplished by detecting and incorporating the expression of certain normalizing biomarkers, including expression products of well-known housekeeping genes. Alternatively, normalization can be based on the mean or median signal of all of the assayed genes or a large subset thereof (global normalization approach). On a gene-by-gene basis, measured normalized amount of a subject tumor mRNA or protein is compared to the amount found in a reference set. Normalized expression levels for each mRNA or protein per tested tumor per subject can be expressed as a percentage of the expression level measured in the reference set. The presence and/or expression level/amount measured in a particular subject sample to be analyzed will fall at some percentile within this range, which can be determined by methods well known in the art.

In certain embodiments, a reference sample, reference cell, reference tissue, control sample, control cell, or control tissue is a single sample or combined multiple samples from the same subject or individual that are obtained at one or more different time points than when the test sample is obtained. For example, a reference sample, reference cell, reference tissue, control sample, control cell, or control tissue is obtained at an earlier time point from the same subject or individual than when the test sample is obtained. Such reference sample, reference cell, reference tissue, control sample, control cell, or control tissue may be useful if the reference sample is obtained before treatment and the test sample is later obtained after treatment.

In certain embodiments, a reference sample, reference cell, reference tissue, control sample, control cell, or control tissue is a combination of multiple samples from one or more healthy individuals who are not the subject or individual. In certain embodiments, a reference sample, reference cell, reference tissue, control sample, control cell, or control tissue is a combination of multiple samples from one or more individuals with a disease or disorder (e.g., cancer) who are not the subject or individual.

In some embodiments, the sample is a clinical sample. In some embodiments, the sample is a liquid biopsy, such as blood. In other embodiments, the sample is a tissue sample, such as a tumor tissue sample (e.g., biopsy tissue) containing T-cells. In some embodiments, the tissue sample is lung tissue. In some embodiments, the tissue sample is renal tissue. In some embodiments, the tissue sample is skin tissue. In some embodiments, the tissue sample is pancreatic tissue. In some embodiments, the tissue sample is gastric tissue. In some embodiments, the tissue sample is bladder tissue. In some embodiments, the tissue sample is esophageal tissue. In some embodiments, the tissue sample is mesothelial tissue. In some embodiments, the tissue sample is breast tissue. In some embodiments, the tissue sample is thyroid tissue. In some embodiments, the tissue sample is colorectal tissue. In some embodiments, the tissue sample is head and neck tissue. In some embodiments, the tissue sample is osteosarcoma tissue. In some embodiments, the tissue sample is prostate tissue. In some embodiments, the tissue sample is ovarian tissue, HCC (liver), blood cells, lymph nodes, and/or bone/bone marrow tissue. In some embodiments, the tissue sample is colon tissue. In some embodiments, the tissue sample is endometrial tissue. In some embodiments, the tissue sample is brain tissue (e.g., glioblastoma, neuroblastoma, and so forth).

In some embodiments, the tumor is a malignant cancerous tumor (i.e., cancer). In some embodiments, the tumor and/or cancer is a solid tumor or a non-solid or soft tissue tumor. Examples of soft tissue tumors include leukemia (e.g., chronic myelogenous leukemia, acute myelogenous leukemia, adult acute lymphoblastic leukemia, acute myelogenous leukemia, mature B-cell acute lymphoblastic leukemia, chronic lymphocytic leukemia, prolymphocytic leukemia, or hairy cell leukemia) or lymphoma (e.g., non-Hodgkin's lymphoma, cutaneous T-cell lymphoma, or Hodgkin's disease). A solid tumor includes any cancer of body tissues other than blood, bone marrow, or the lymphatic system. Solid tumors can be further divided into those of epithelial cell origin and those of non-epithelial cell origin. Examples of epithelial cell solid tumors include tumors of the gastrointestinal tract, colon, colorectal (e.g., basaloid colorectal carcinoma), breast, prostate, lung, kidney, liver, pancreas, ovary (e.g., endometrioid ovarian carcinoma), head and neck, oral cavity, stomach, duodenum, small intestine, large intestine, anus, gall bladder, labium, nasopharynx, skin, uterus, male genital organ, urinary organs (e.g., urothelium carcinoma, dysplastic urothelium carcinoma, transitional cell carcinoma), bladder, and skin. Solid tumors of non-epithelial origin include sarcomas, brain tumors, and bone tumors. In some embodiments, the cancer is non-small cell lung cancer (NSCLC). In some embodiments, the cancer is second-line or third-line locally advanced or metastatic non-small cell lung cancer. In some embodiments, the cancer is adenocarcinoma. In some embodiments, the cancer is squamous cell carcinoma. In some embodiments, the cancer is non-small cell lung cancer (NSCLC), glioblastoma, neuroblastoma, melanoma, breast carcinoma (e.g. triple-negative breast cancer), gastric cancer, colorectal cancer (CRC), or hepatocellular carcinoma. In some embodiments, the cancer is a primary tumor. In some embodiments, the cancer is a metastatic tumor at a second site derived from any of the above types of cancer.

In some embodiments, the at least one response to therapy biomarker is/are detected in the sample using a method selected from the group consisting of FACS, Western blot, ELISA, immunoprecipitation, immunohistochemistry, immunofluorescence, radioimmunoassay, dot blotting, immunodetection methods, HPLC, surface plasmon resonance, optical spectroscopy, mass spectrometry, HPLC, qPCR, RT-qPCR, multiplex qPCR or RT-qPCR, RNA-seq, microarray analysis, SAGE, MassARRAY technique, and FISH, and combinations thereof. In some embodiments, the at least one response to therapy biomarker is/are detected using FACS analysis or immunofluorescence microscopy. In some embodiments, the at least one response to therapy biomarker is detected in blood samples. In some embodiments, the at least one response to therapy biomarker is detected in $CD8^+$ T-cell obtained from blood samples. Any suitable method to isolate/enrich such population of cells may be used including, but not limited to, cell sorting. In some embodiments, EOMES-641K-Ac expression is reduced in samples from individuals that respond to treatment with a therapy, suitably an immunotherapy (e.g., one that comprises an anti-immune checkpoint molecule antibody). In some embodiments, EOMES-641K-Ac expression is elevated in samples from individuals that do not respond or respond weakly to treatment with a therapy, suitably an immunotherapy (e.g., one that comprises an anti-immune checkpoint molecule antibody). In some embodiments, EOMES-641K-Me and/or EOMES-373K-Me expression is reduced in samples from individuals that do not respond or weakly respond to treatment with a therapy, suitably an immunotherapy (e.g., one that comprises an anti-immune checkpoint molecule antibody). In some embodiments, EOMES-641K-Me and/or EOMES-373K-Me expression is elevated in samples from individuals that respond to treatment with a therapy, suitably an immunotherapy (e.g., one that comprises an anti-immune checkpoint molecule antibody). IN particular examples, the ratio of biomarkers is assessed, e.g. the ratio of EOMES-641K-Ac to EOMES-641K-Me, or vis versa.

In some embodiments, the expression level of one or more biomarkers may be compared to a reference which may include, for example, a sample comprising functional or competent T-cells, a sample comprising dysfunctional or exhausted T-cells, a sample from a subject who does not have cancer, or a sample from a subject with cancer but not receiving a therapy (e.g., a cytotoxic therapy or an immunotherapy). In some embodiments, a reference may include a reference value from multiple subjects or samples. For example, a mean, average, or median value for expression level of the at least one response to therapy biomarker may be generated from a population of healthy subjects, subjects who respond to therapy or subjects who do not respond to therapy, or from multiple samples of T-cells of known immune function, as a whole. A set of samples obtained from cancers having a shared characteristic (e.g., the same cancer type and/or stage, or exposure to a common therapy) may be studied from a population, such as with a clinical outcome study. This set may be used to derive a reference, e.g., a reference number, to which a subject's sample may be compared.

Certain aspects of the present disclosure relate to measurement of the expression level of one or more biomarkers (e.g., gene expression products including mRNAs and proteins) in a sample comprising T-cells. In some embodiments, the sample may be a peripheral blood sample (e.g., from a patient with cancer). In some embodiments, the sample is a tumor sample. In some embodiments, the sample may be processed to separate or isolate one or more cell types (e.g., $CD8^+$ T-cells). In some embodiments, the sample may be used without separating 25 or isolating cell types.

A tumor sample may be obtained from a subject by any method known in the art, including without limitation a biopsy, endoscopy, or surgical procedure. In some embodiments, a tumor sample may be prepared by methods such as freezing, fixation (e.g., by using formalin or a similar fixative), and/or embedding in paraffin wax. In some embodiments, a tumor sample may be sectioned. In some embodiments, a fresh tumor sample (i.e., one that has not been prepared by the methods described above) may be used. In some embodiments, a peripheral blood sample may be prepared by incubation in a solution to preserve mRNA and/or protein integrity.

In some embodiments, the sample may be a peripheral blood sample. A peripheral blood sample may include white blood cells, PBMCs, and the like. Any technique known in the art for isolating leukocytes from a peripheral blood sample may be used. For example, a blood sample may be drawn, red blood cells may be lysed, and a white blood cell pellet may be isolated and used for the sample. In another example, density gradient separation may be used to separate leukocytes (e.g., PBMCs) from red blood cells. In some embodiments, a fresh peripheral blood sample (i.e., one that has not been prepared by the methods described above) may be used. In some embodiments, a peripheral blood sample may be prepared by incubation in a solution to preserve mRNA and/or protein integrity.

In some embodiments, responsiveness to therapy may refer to any one or more of: extending survival (including overall survival and progression free survival); resulting in an objective response (including a complete response or a partial response); or improving signs or symptoms of cancer. In some embodiments, responsiveness may refer to improvement of one or more factors according to the published set of RECIST guidelines for determining the status of a tumor in a cancer patient, i.e., responding, stabilizing, or progressing. For a more detailed discussion of these guidelines, see, Eisenhauer et al. (2009 *Eur J Cancer* 45:228-47), Topalian et al. (2012 *N Engl J Med* 366:2443-54), Wolchok et al. (2009 *Clin Can Res* 15:7412-20) and Therasse et al. (2000 *J. Natl. Cancer Inst.* 92:205-16). A responsive subject may refer to a subject whose cancer(s) show improvement, e.g., according to one or more factors based on RECIST criteria. A non-responsive subject may refer to a subject whose cancer(s) do not show improvement, e.g., according to one or more factors based on RECIST criteria.

Conventional response criteria may not be adequate to characterize the anti-tumor activity of therapeutic agents of the invention, which can produce delayed responses that may be preceded by initial apparent radiological progression, including the appearance of new lesions. Therefore, modified response criteria have been developed that account for the possible appearance of new lesions and allow radiological progression to be confirmed at a subsequent assessment. Accordingly, in some embodiments, responsiveness may refer to improvement of one of more factors according to immune-related response criteria (irRC). See, e.g., Wolchok et al. (2009, supra). In some embodiments, new lesions are added into the defined tumor burden and followed, e.g., for radiological progression at a subsequent assessment. In some embodiments, presence of non-target lesions is included in assessment of complete response and not included in assessment of radiological progression. In some embodiments, radiological progression may be determined only on the basis of measurable disease and/or may be confirmed by a consecutive assessment ≥4 weeks from the date first documented.

In some embodiments, responsiveness may include immune activation. In some embodiments, responsiveness may include treatment efficacy. In some embodiments, responsiveness may include immune activation and treatment efficacy.

3. Biomarker Panels

The biomarkers of the present invention can be used in predictive and/or prognostic tests to assess, determine, and/or qualify (used interchangeably herein) response to therapy signature status in a patient and therefore, direct treatment of the patient. The phrase "response to therapy signature status" includes a high response to therapy signature (RT high) and a low response to therapy signature (RT low). Based on this status, further procedures may be indicated, including additional tests or therapeutic procedures or regimens.

The response to therapy signature panel suitably includes one or more of EOMES-641K-Ac, EOMES-641K-Me and/or EOMES-373K-Me. It is understood that any one or more other biomarkers may also be included in the panel, such as, for example, IFN-γ, TNF-α, IL-2, Ki67, PD-1 and/or CD107a.

The power of an assay to correctly predict response to therapy is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1−specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker signatures of the present invention may show a statistical difference in different response to therapy statuses of at least $p<0.05$, $p<10^{-2}$, $p<10^{-3}$, $p<10^{-4}$ or $p<10^{-5}$. Predictive or prognostic tests that use these biomarkers may show an ROC of at least 0.6, at least about 0.7, at least about 0.8, or at least about 0.9.

In certain embodiments, the biomarkers are measured in a patient sample using the methods described herein and a response to therapy signature status is calculated. In particular embodiments, the measurement(s) may then be compared with a relevant predictive or prognostic amount(s), cut-off(s), or multivariate model scores that distinguish a high therapy response signature (RT high) status from a low therapy response signature (RT low) status. The predictive or prognostic amount(s) represents a measured amount of a biomarker(s) above which or below which a patient is classified as having a particular therapy response signature status. As is well understood in the art, by adjusting the particular predictive or prognostic cut-off(s) used in an assay, one can increase sensitivity or specificity of the assay depending on the preference of the skilled person. In particular embodiments, the particular predictive or prognostic cut-off can be determined, for example, by measuring the level or amount of biomarkers in a statistically significant number of samples from patients with different response to therapy signature statuses, and drawing the cut-off to suit the desired levels of specificity and sensitivity.

Furthermore, in certain embodiments, the values measured for biomarkers of a biomarker panel are mathematically combined and the combined value is correlated to the underlying predictive or prognostic question of high or low response to therapy signature. Biomarker values may be combined by any appropriate mathematical method known in the art. Well-known mathematical methods for correlating a biomarker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in a correlating a biomarker combination of the present invention is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

4. Generation of Classification Algorithms for Qualifying Response to Therapy Signature Status In some embodiments, data that are generated using samples such as "known samples" can then be used to "train" a classification model. A "known sample" is a sample that has been pre-classified. The data that are used to form the classification model can be referred to as a "training data set". The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition.

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application No. 2002 0138208 A1 to Paulse et al., "*Method for analyzing mass spectra.*"

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al., "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows® or Linux™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, $C^{++}$, visual basic, etc.

The learning algorithms described above are useful both for developing classification algorithms for the biomarkers already discovered, and for finding new biomarker biomarkers. The classification algorithms, in turn, form the base for diagnostic tests by providing diagnostic values (e.g., cut-off points) for biomarkers used singly or in combination.

In some embodiments any of the classification methods disclosed herein may be performed at least in part by one or more computers and/or may be stored in a database on a non-transitory computer medium. In some embodiments any of the classification methods disclosed herein may be embodied or stored at least in part on a computer-readable medium having computer-executable instructions thereon. In some embodiments a computer-readable medium comprises any non-transitory and/or tangible computer-readable medium.

5. Antibodies and Cell Lines

The present invention discloses the localization, detection and quantitation of response to therapy biomarkers, particularly EOMES-641K-Ac, EOMES-641K-Me and/or EOMES-373K-Me, using antigen-binding molecules that bind specifically to these biomarkers. Such antigen-binding molecules are typically isolated acetylation or methylation site-specific antigen-biding molecules that bind specifically to EOMES only when 641K is acetylated or methylated, or when 373K is methylated. Such antigen-binding molecules may be produced by standard antibody production methods, such as anti-peptide antibody methods, using the acetylation and methylation site sequence information provided herein, and as described for example in the examples. For example, an antibody that binds specifically to EOMES-641K-Ac, EOMES-641K-Me or EOMES-373K-Me can be produced by immunizing an animal with a peptide antigen comprising all or part of the amino acid sequence encompassing the respective acetylated or methylated residue (e.g., a peptide antigen comprising the sequence set forth in SEQ ID NO: 3, 4 or 5 (which encompasses the acetylated or methylated lysine (suitably, dimethyl lysine) at position 641 or EOMES, and the methylated lysine (suitably, dimethyl lysine) at position 373 of EOMES), to produce an antibody that only binds EOMES when acetylated or methylated at position 641 or methylated at position 373.

Polyclonal antibodies of the invention may be produced according to standard techniques by immunizing a suitable animal (e.g., rabbit, goat, etc.) with a peptide antigen corresponding to the protein acetylation or methylation site of interest, collecting immune serum from the animal, and separating the polyclonal antibodies from the immune serum, in accordance with standard procedures. For example, if an antibody that only binds EOMES when acetylated or methylated at 641K is desired, the peptide antigen includes the acetylated or methylated form of lysine (e.g., K (Ac) or K (Me2), respectively). Conversely, if an antibody that only binds EOMES when not acetylated or methylated at 641K is desired, the peptide antigen includes the non-acetylated and non-methylated, conventional form of lysine.

Peptide antigens suitable for producing antibodies of the invention may be designed, constructed and employed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, Methods In Enzymology, 201:264-283 (1991); Merrifield, J. Am. Chem. Soc. 85:21-49 (1962)).

It will be appreciated by those of skill in the art that longer or shorter acetylpeptide or methylpeptide antigens may be employed. For example, a peptide antigen may comprise an amino acid sequence set forth in any one of SEQ ID NOs: 3, 4 or 5, or it may comprise additional amino acids flanking that sequence, or may comprise only a portion of the disclosed sequence immediately flanking the acetylatable or methylatable lysine. Typically, a desirable peptide antigen will comprise four or more amino acids flanking each side of the acetylatable or methylatable amino acid and encompassing it. Polyclonal antibodies produced as described herein may be screened as further described below.

Monoclonal antibodies of the invention may be produced in a hybridoma cell line according to the well-known technique of Kohler and Milstein. See Nature 265:495-97 (1975); Kohler and Milstein, Eur. J. Immunol. 6:511 (1976); see also, CURRENT PROTOCOLS IN MOLECULAR BIOLOGY, Ausubel et al. Eds. (1989). Monoclonal antibodies so produced are highly specific, and improve the selectivity and specificity of diagnostic assay methods provided by the invention. For example, a solution containing the appropriate antigen may be injected into a mouse or other species and, after a sufficient time (in keeping with conventional techniques), the animal is sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S. Pat. No. 5,675,063, C. Knight, Issued Oct. 7, 1997. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, *Science* 246:1275-81 (1989); Mullinax et al., *Proc. Nat'l Acad. Sci.* 87:8095 (1990). If monoclonal antibodies of one isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.,* 82:8653 (1985); Spira et al., *J. Immunol. Methods,* 74:307 (1984)).

The preferred epitope of an acetylation-site specific antibody or methylation-site specific antibody of the invention is a peptide fragment consisting essentially of about 8 to 17 amino acids including the acetylatable or methylatable lysine, wherein about 3 to 8 amino acids are positioned on each side of the acetylatable lysine, and antibodies of the invention thus specifically bind to a post-translationally modified EOMES polypeptide comprising such epitopic sequence. Particularly preferred epitopes bound by the antibodies of the invention comprise all or part of an acetylatable or methylatable site sequence, including the acetylatable or methylatable amino acid.

Included within the scope of the present invention are equivalent non-antibody molecules, such as antigen-binding fragments, which bind, in a acetyl- or methyl-specific manner, to essentially the same acetylatable or methylatable epitope to which the acetyl- or methyl-specific antigen-binding molecules of the invention bind. See, e.g., Neuberger et al., *Nature* 312:604 (1984). Such equivalent non-antibody reagents may be suitably employed in the methods of the invention further described below.

Antigen-binding molecules contemplated by the invention may be any type of antibody including immunoglobulins, including IgG, IgM, IgA, IgD, and IgE, and antigen-binding fragments thereof. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26:403-11 (1989); Morrision et al., *Proc. Nat'l. Acad. Sci.* 81:6851 (1984); Neuberger et al., *Nature* 312:604 (1984)). The antibodies may be recombinant monoclonal antibodies produced according to the methods disclosed in U.S. Pat. No. 4,474,893 (Reading) or U.S. Pat. No. 4,816,567 (Cabilly et al.) The antibodies may also be chemically constructed by specific antibodies made according to the method disclosed in U.S. Pat. No. 4,676,980 (Segel et al.).

The invention also provides immortalized cell lines that produce an antibody of the invention. For example, hybridoma clones, constructed as described above, that produce monoclonal antibodies to the EOMES acetylation or methylation sites disclosed herein are also provided. Similarly, the invention includes recombinant cells producing an antibody of the invention, which cells may be constructed by well-known techniques; for example the antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

Acetylation or methylation site-specific antibodies of the invention, whether polyclonal or monoclonal, may be screened for epitope and acetyl- or methyl-specificity according to standard techniques. See, e.g. Czemik et al., *Methods in Enzymology,* 201:264-283 (1991). For example, the antibodies may be screened against the acetyl and non-acetyl peptide library by ELISA to ensure specificity for both the desired antigen and for reactivity only with the acetylated or methylated (or non-acetylated, non-methylated) form of the antigen. Peptide competition assays may be carried out to confirm lack of reactivity with other acetyl-epitopes on the given protein acetylation signaling protein. The antibodies may also be tested by Western blotting against cell preparations containing the signaling protein, e.g. cell lines over-expressing the target protein, to confirm reactivity with the desired acetylated epitope/target.

Specificity against the desired acetylated or methylated epitope may also be examined by constructing mutants lacking acetylatable or methylatable residues at positions outside the desired epitope that are known to be acetylated, or by mutating the desired acetyl- or methyl epitope and confirming lack of reactivity. Acetylation- or methylation-site specific antigen-binding molecules of the invention may exhibit some limited cross-reactivity to related epitopes in non-target proteins. This is not unexpected as most antigen-binding molecules exhibit some degree of cross-reactivity, and anti-peptide antibodies will often cross-react with epitopes having high homology to the immunizing peptide. See, e.g., Czemik, supra. Cross-reactivity with non-target proteins is readily characterized by Western blotting along-side markers of known molecular weight. Amino acid sequences of cross-reacting proteins may be examined to identify sites highly homologous to the EOMES epitope for which the antigen-binding molecules of the invention are specific.

In certain cases, polyclonal antisera may exhibit some undesirable general cross-reactivity to acetyl-lysine or methyl-lysine (suitably, dimethyl lysine) itself, which may be removed by further purification of antisera, e.g., over an acetyltyramine or methyltyramine column. Antigen-binding molecules of the invention specifically bind EOMES only when acetylated or only when methylated (or only when not acetylated and not methylated, as the case may be) at 641K or 373K, and do not (substantially) bind to the other form (as compared to the form for which the antigen-binding molecule is specific).

Antigen-binding molecules may be further characterized via IHC or IF using normal and dysfunctional (e.g. exhausted) T-cells to examine EOMES acetylation or methylation. IHC or IF may be carried out according to well-known techniques. See, e.g., ANTIBODIES: A LABORATORY MANUAL, Chapter 10, Harlow & Lane Eds., Cold Spring Harbor Laboratory (1988). For example, briefly, paraffin-embedded tissue (e.g., tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions. IF may be performed, for example, essentially as described below in the examples Antigen-binding molecules may be further characterized by flow cytometry carried out according to standard methods. See Chow et al., Cytometry (Communications in Clinical Cytometry) 46:7205-238 (2001). Briefly and by way of example, the following protocol for cytometric analysis may be employed: samples may be centrifuged on Ficoll gradients to remove erythrocytes, and cells may then be fixed with 2% paraformaldehyde for 10 minutes at 37.degree. C. followed by permeabilization in 90% methanol for 30 minutes on ice. Cells may then be stained with the primary acetylation- or methylation-site specific antigen-binding molecule of the invention (which detects, for example, EOMES-641K-Ac, EOMES-641K-Me or EOMES-373K-Me), washed and labeled with a fluorescent-labeled secondary antibody. Additional fluorochrome-conjugated biomarker antibodies (e.g., IFN-γ, TNF-α, IL-2, Ki67, PD-1 and/or CD107a) may also be added at this time to aid in the assessment of T-cell function. The cells may then be analyzed on a flow cytometer according to the specific protocols of the instrument used.

Antigen-binding molecules may be advantageously conjugated to fluorescent dyes (e.g., Alexa Fluor 488) for use in multi-parametric analyses.

Acetylation- or methylation-site specific antigen-binding molecules of the invention specifically bind to human EOMES polypeptide, only when acetylated or methylated at 641K or methylated at 373K, but are not limited only to binding the human species, per se. The invention includes antigen-binding molecules that also bind conserved and highly homologous or identical acetylation or methylation sites in respective EOMES proteins from other species (e.g., mouse, rat, monkey, yeast), in addition to binding the human acetylation or methylation site. Highly homologous or identical sites conserved in other species can readily be identified by standard sequence comparisons, such as using BLAST, with the human EOMES acetylation and methylation sites disclosed herein.

6. Kits

The present invention also extends to kits for determining expression of biomarkers, including the response to therapy biomarkers and other biomarkers disclosed herein, which include reagents that allow detection and/or quantification of the biomarkers. Such reagents include, for example, compounds or materials, or sets of compounds or materials, which allow quantification of the biomarkers. In specific embodiments, the compounds, materials or sets of compounds or materials permit determining the expression level of a protein or the expression level of a gene, including without limitation, antigen-binding molecules (e.g. antibodies), material for extraction of RNA, primers for the synthesis of a corresponding cDNA, primers for amplification of DNA, and/or probes capable of specifically hybridizing with the RNAs (or the corresponding CDNAs) encoded by the genes, TaqMan probes, etc.

The kits may also optionally include appropriate reagents for detection of labels, positive and negative controls, washing solutions, blotting membranes, microtiter plates, dilution buffers and the like. For example, a protein-based detection kit may include (i) at least one EOMES polypeptide, which is suitably selected from EOMES-641K-Ac, EOMES-641K-Me and/or EOMES-373K-Me, or fragments thereof that comprise 641K-Ac, 641K-Me or 373K-Me, and an EOMES polypeptide that is not acetylated or methylated (which may be used as a control), and (ii) one or more antigen-binding molecules that bind specifically to a EOMES polypeptide (e.g. EOMES-641K-Ac, EOMES-641K-Me and/or EOMES-373K-Me, and/or an EOMES polypeptide that is not acetylated or methylated). The antigen-binding molecules are suitably detectably labeled. The kit can also feature various devices (e.g., one or more) and reagents (e.g., one or more) for performing one of the assays described herein; and/or printed instructional material for using the kit to quantify the expression of a T-cell function biomarker gene.

Materials suitable for packing the components of the diagnostic kits may include crystal, plastic (polyethylene, polypropylene, polycarbonate and the like), bottles, vials, paper, envelopes and the like. Additionally, the kits of the invention can contain instructional material for the simultaneous, sequential or separate use of the different components contained in the kit. The instructional material can be in the form of printed material or in the form of an electronic support capable of storing instructions such that they can be read by a subject, such as electronic storage media (magnetic disks, tapes and the like), optical media (CD-ROM, DVD)

and the like. Alternatively or in addition, the media can contain Internet addresses that provide the instructional material.

7. Patient Classification and Treatment Management

The present invention extends to methods of selecting or identifying individuals who are appropriate candidates for treatment with a therapy (e.g., a cytotoxic therapy, an immunotherapy, etc.) for treatment of cancer. Such individuals include patients that are predicted to be responsive to the therapy and thus have an increased likelihood of benefiting from administration of the therapy relative to other patients having different characteristic(s) (e.g., non-responsiveness to the therapy). In certain embodiments an appropriate candidate is one who is reasonably likely to benefit from treatment or at least sufficiently likely to benefit as to justify administering the treatment in view of its risks and side effects. The invention also encompasses methods of selecting or identifying individuals who are not appropriate candidates for treatment with a therapy (e.g., a cytotoxic therapy, an immunotherapy, etc.) for treatment of cancer. Such individuals include patients that are predicted to be non-responsive or weakly responsive to the therapy and thus have a decreased likelihood of benefiting from administration of the therapy relative to other patients having different characteristic(s) (e.g., responsiveness to the therapy), or a low or substantially no likelihood of benefiting from such treatment, such that it may be desirable to use a different or additional treatment. In some embodiments, whether a subject is an appropriate candidate for therapy with a therapy is determined based on an assay of at least one response to therapy biomarker in a sample obtained from the subject.

In some aspects, described herein are methods of determining, for example based on an assay of at least one response to therapy biomarker, the likelihood that a subject in need of treatment for cancer will respond to treatment with a therapy (e.g., a cytotoxic therapy, an immunotherapy, etc.) and/or of identifying and/or selecting a subject to receive such treatment. In specific embodiments, the therapy is an immunotherapy, suitably with an anti-immune checkpoint inhibitor. The phrase "treatment with an immune checkpoint inhibitor", also referred to as "immune checkpoint inhibitor treatment", "therapy with an immune checkpoint inhibitor", or "immune checkpoint inhibitor therapy", encompasses embodiments pertaining to treatment with a single immune checkpoint inhibitor and embodiments pertaining to treatment with two or more immune checkpoint inhibitors in combination. In some embodiments immune checkpoint inhibitor treatment comprises inhibiting two or more different immune checkpoint pathways using a single agent or using two or more separate agents.

The present invention also encompasses the use of methods for assessing T-cell function or the immune function of a subject described herein in methods of selecting or identifying individuals with impaired or reduced immune function for treatment with a therapy (e.g., an immunotherapy such as adoptive immunotherapy) that stimulates or enhances immune function.

In order that the invention may be readily understood and put into practical effect, particular preferred embodiments will now be described by way of the following non-limiting examples.

EXAMPLES

Example 1

Eomes Expression in T-Cells

To quantify the functional nature of $CD8^+$ T-cells from stage IV metastatic melanoma cancer, liquid biopsies, which are a vital tool to quantify the phenotypes of immune cells in the blood, were acquired from melanoma patients that were stratified based on RECIST 1.1 (which classifies response to therapy based on tumour mass change; Eisenhauer et al., Eur J Cancer. 2009, 45 (2): 228-47), patients with metastatic breast cancer and healthy individuals. Patient subgroups included those classified as patients with complete response (CR), partial response (PR), stable disease (SD) or progressive disease (PD). Briefly, $CD8^+$ T-cells were isolated from liquid biopsies of healthy donors (HD), patients with metastatic breast cancer or patients with melanoma every 3 months for 24 months after a baseline bleed. Melanoma patients were further classified based on objective response to immunotherapy treatment (either mono or dual therapy using Pembrolizumab, Nivolumab and/or Ipilimumab) into complete response (CR), partial response (PR), stable disease (SD) or progressive disease (PD).

Analysis was carried out either prior to or following stimulation of the $CD8^+$ T-cells to promote expression of effector markers, and protein expression was analysed by high resolution immunofluorescence. Dysfunctional/exhausted $CD8^+$ T-cells fail to express effector proteins (Huang et al., 2017, Nature, 545 (7652), 60-65; Wherry and Kurachi 2015, Nat Rev Immunol, 15 (8), 486-499; Bengsch et al., 2018, Immunity, 48 (5), 1029-1045; Catakovic et al., 2017, Cell Commun Signal, 15 (1), 1; Woroniecka et al., 2018 Clin Cancer Res, 24 (17), 4175-4186). Analysis of the T-cells in this study showed that, relative to CR and SD melanoma cohorts, the PD cohort had low expression of Ki67, TNF-α and IFN-γ, with no effect observed upon stimulation (FIG. 1A).

Next, $CD8^+$ T-cells derived from the same patient cohorts that were demonstrated above to be dysfunctional were probed for expression of the proposed exhaustion signature, PD-1 and EOMES. PD-1 was included because it is the major inhibitory check point shown in dysfunctional T-cells. Analysis revealed that $CD8^+$ T-cells derived from the melanoma PD cohort had significant and strikingly higher nuclear EOMES expression that those of the HD, CR, PR cohorts (FIG. 1B).

Due to the importance of EOMES in exhausted, dysfunctional T-cells, the EOMES sequence was examined for a putative nuclear localisation signal using NLS mapper and online tool for identifying potential methylation residues. A sequence at the C-terminus was identified as having a high likelihood of mediating nuclear localization (FIG. 1C). This region was identified as $^{635}$VYTSACKRRRLSP$^{647}$, and the lysine (K) at position 641 (641K) was identified as been a potential target of methylation/de-methylation and as a target for acetylation based on the tool prediction of species-specific methylation sites and acetylation sites (Wen et al., 2016, *Bioinformatics,* 32 (20), 3107-3115). Many studies have demonstrated the importance of a variety of post-translational modifications to control protein-target interactions and localisations. Therefore, it was hypothesized that the methylation, de-methylation and acetylation of this lysine within the EOMES NLS may be critical in regulating its nuclear localisation and dynamics.

To understand the importance of post-translational modification of EOMES at 641K, three 3 plasmid constructs were made (FIG. 1D). E-WT, which represents the wild-type EOMES sequence; E-MUT1, in which 641K is mutated to an arginine (R), thus mimicking a lysine that is in a unmethylated, unacetylated state; and E-MUT2, in which 641K is mutated to a phenylalanine, thus mimicking a hypermethylated state of lysine. As E-MUT1 is not able to be methylated or acetylated, this construct was used to indicate the importance of acetylation and methylation in nuclear entry, with the hypothesis being that nuclear entry dynamics would be altered by this mutation. The mutation in E-MUT2 should render the EOMES polypeptide incapable of nuclear localisation.

It was observed that a functional lysine at position 641 that can be de-methylated is required for nuclear translocation of EOMES to the nucleus, while hypermethylation of EOMES at 641K resulted in a reduction of nuclear EOMES. Specifically, the effect of transfection of Jurkat cells with E-WT, E-MUT1 and E-MUT2 on EOMES, TBET and PD-1 was examined, with the results shown in FIG. 1E. High resolution microscopy found that, relative to E-WT, localization of EOMES in cells transfected with E-MUT1 or E-MUT2 was significantly more biased to the cytoplasm, with significantly lower nuclear EOMES and lower nuclear bias (as shown with the ratio of fluorescence in the nucleus relative to the cytoplasm: Fn/c) (FIG. 1E). In comparison to the vector only control, the EOMES expression in cells transfected with E-MUT1 was slightly lower but not significantly so, whereas the Fn/c of EOMES was still cytoplasmically biased compared to the vector only control. In cells transfected with E-MUT2, the mean NFI and EOMES Fn/c was significantly lower than observed with the vector-only control. TBET expression was slightly increased by transfection of E-WT, while transfection of E-MUT1 of E-MUT2 induced higher expression of nuclear TBET compared to both the vector-only control and E-WT. PD-1 expression was unaffected by transfection with E-WT but both E-MUT1 and E-MUT2 transfection abrogated PD-1 expression significantly.

These data suggest that the constitutive methylation of 641K (as represented by E-MUT2) has a different effect on cellular localization and protein expression than non-methylation/non-acetylation of 641K (as represented by E-MUT1). This is potentially due to the effect methylation at 641K may have on the protein interaction of EOMES, resulting in differing interactions and differing effects on expression of proteins. This indicates the importance of de-methylation of 641K in influencing nuclear targeting and protein:protein interaction of EOMES.

The effect of transfection of E-WT, E-MUT1 and E-MUT2 on expression of Ki67, IFN-γ and TNF-α was examined in the same set of transfected Jurkat cells as described above. High resolution microscopy analysis revealed that transfection of E-WT significantly abrogated expression of Ki67, IFN-γ and TNF-α in comparison to vector only control or E-WT. Transfection of E-MUT1 induced significantly higher expression of Ki67 and IFN-γ, but not TNF-α, relative to the control, but expression of these proteins was significantly higher when compared to E-WT transfected cells. Transfection of E-MUT2 had a significant and strong effect on the expression of all three proteins, with much higher expression observed than in cells transfected with the control, E-WT or E-MUT1 (FIG. 1F).

This data suggests that nuclear localization EOMES is required to abrogate expression of effector markers, as indicated by E-WT abrogation of Ki67, IFN-γ and TNF-α. However, it was also found that hypermethylated EOMES was able to induce strong expression of Ki67, IFN-γ and TNF-α. This suggests that different post-translational modifications of EOMES at critical residues may, in addition to having an effect on localization, also induce different protein interactions as seen by the differences between E-MUT1 and E-MUT2 induced expression of effector proteins. It can therefore be concluded that the specific post-translational modification present at 641K in EOMES is important in regulating the protein targets of EOMES as well as protein: target interactions and nuclear localisation.

Example 2

Figure 2:
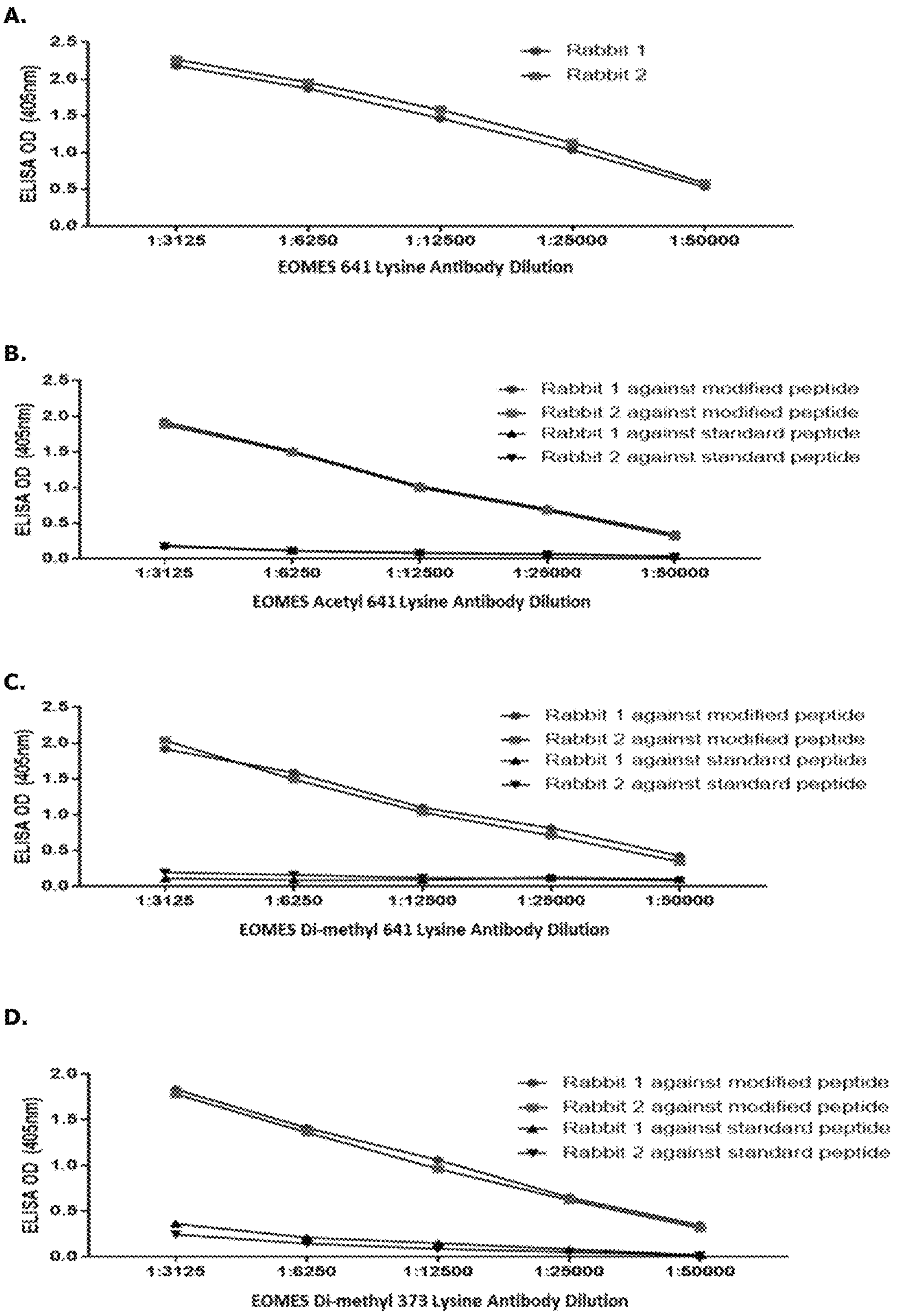
FIG. 2 is a graphical representation of the specificity of polyclonal rabbit antibodies raised against various EOMES polypeptides. (A) Antibodies raised against EOMES polypeptide with no post-translational modification. (B) Antibodies raised against EOMES polypeptide with acetylation at the lysine at position 641. (C) Antibodies raised against EOMES polypeptide with methylation at the lysine at position 641. (D) Antibodies raised against EOMES polypeptide with methylation at the lysine at position 373.

Antibodies Specific to Post-Translationally Modified Eomes can Predict Responsiveness to Therapy To investigate the effect of post-translational modification of 641K in the EOMES polypeptide, rabbit polyclonal antibodies specific for the NLS motif where raised against 641K-methylated, and 641K acetylated EOMES protein (i.e. EOMES-641K-Me and EOMES-641K-Ac). FIG. 2 shows the specificity of the antibodies.

Figure 3:
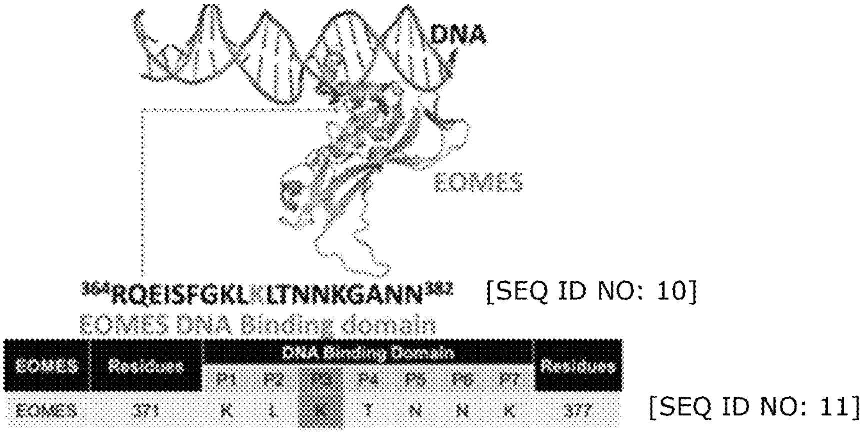
FIG. 3 is a schematic and graphical representation showing the ability of anti-EOMES antibodies to predict patient response to immunotherapy. (A) EOMES protein structure showing the DNA binding domain. (B) Schematic of production of polyclonal antibodies specific for the NLS motif or DNA binding motif, either unmodified or modified by methylation (Me) or acetylation (Ac). (C) Melanoma patient formalin-fixed paraffin-embedded (FFPE) samples from the primary tumor baseline biopsy classified eventually as a responder or a resistant cohort were processed for 3D high resolution microscopy using the BOND RX (Leica Biosystems). FFPE tissues were fixed and immunofluorescence microscopy was performed by probing the samples with primary antibodies to CD8, acetylated EOMES (anti-EOMES-641K-Ac; "EOMES-Ac") or methylated EOMES (anti-EOMES-641K-Me; "EOMES-Me") with DAPI staining. Graphs plots represent the average NFI values for EOMES-Me and mean NFI for EOMES-Ac, measured using ImageJ minus background (N=90 cells per a patient sample. With N=10 patients a cohort). (D) Liquid biopsies were taken from consenting melanoma patients every 3 months for 24 months after a baseline bleed. Patients were further classified as resistant or responsive to immunotherapy based on objective response to immunotherapy treatment (either mono or dual therapy using Pembrolizumab, Nivolumab and/or Ipilimumab). $CD8^+$ T-cells isolated from blood from either a resistant cohort or a responder cohort defined as per RECIST 1.1 were screened with anti-CD8 antibody and the anti-EOMES-641K-Ac polyclonal antibodies. Cells were fixed and immunofluorescence microscopy was performed with the antibodies and DAPI staining. Graphs plots represent the mean NFI and Cytoplasmic Fluorescent Intensity (CFI) for EOMES-641K-Ac measured using ImageJ minus background (n=10 patients per a group) for N=10 patients a cohort. (E) Liquid biopsies were taken from consenting melanoma patients every 3 months for 24 months after a baseline bleed. Patients were further classified as resistant or responsive to immunotherapy based on objective response to immunotherapy treatment (either mono or dual therapy using Pembrolizumab, Nivolumab and/or Ipilimumab). $CD8^+$ T-cells isolated from blood from either a resistant cohort or a responder cohort defined as per RECIST 1.1 were screened with an anti-CD8 antibody and the anti-EOMES-641K-Me polyclonal antibodies. Cells were fixed and immunofluorescence microscopy was performed with the antibodies and DAPI staining. Graph plots represent the mean NFI, CFI for EOMES-641K-Me measured using ImageJ minus background (n=10 patients per a group). (F) Liquid biopsies were taken from consenting melanoma patients every 3 months for 24 months after a baseline bleed. Patients were further classified as resistant or responsive to immunotherapy based on objective response to immunotherapy treatment (either mono or dual therapy using Pembrolizumab, Nivolumab and/or Ipilimumab). $CD8^+$ T-cells isolated from blood from either a resistant cohort or a responder cohort defined as per RECIST 1.1 were screened with an anti-CD8 antibody and the anti-EOMES-373K-Me polyclonal antibodies. Cells were fixed and immunofluorescence microscopy was performed with the antibodies and DAPI staining. Graph plots represent the mean NFI, CFI for EOMES-373K-Me measured using ImageJ minus background (n=10 patients per a group). (G) Liquid biopsies taken from consenting patients with BRACA positive, triple negative breast cancer (TNBC) every 1 month for 12 months after a baseline bleed. $CD8^+$ T-cells isolated from blood from either a resistant cohort or a responder cohort defined as per RECIST 1.1 were screened with an anti-CD8 antibody, the anti-EOMES-641K-Me polyclonal antibodies or the anti-EOMES-641K-Ac polyclonal antibodies. Cells were fixed and immunofluorescence microscopy was performed with the antibodies and DAPI staining. Graph plots represent the mean FI for EOMES-641K-Ac and FI for EOMES-641K-Me measured using ImageJ minus background (n=10 patients per a group).
Figure 3:
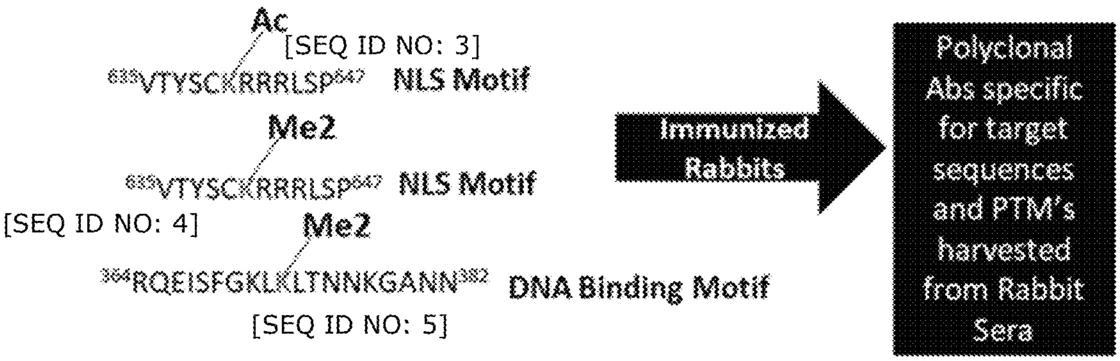
Figure 3:
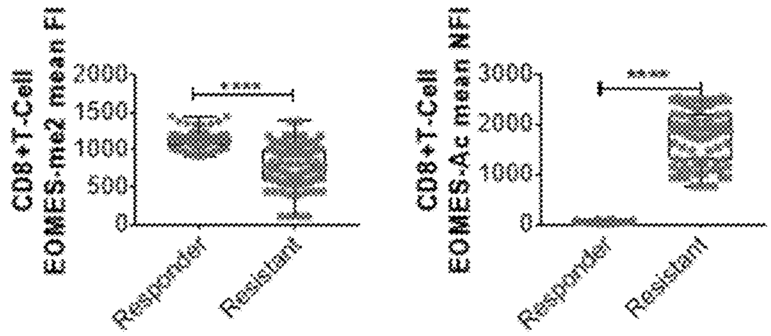
Figure 3:
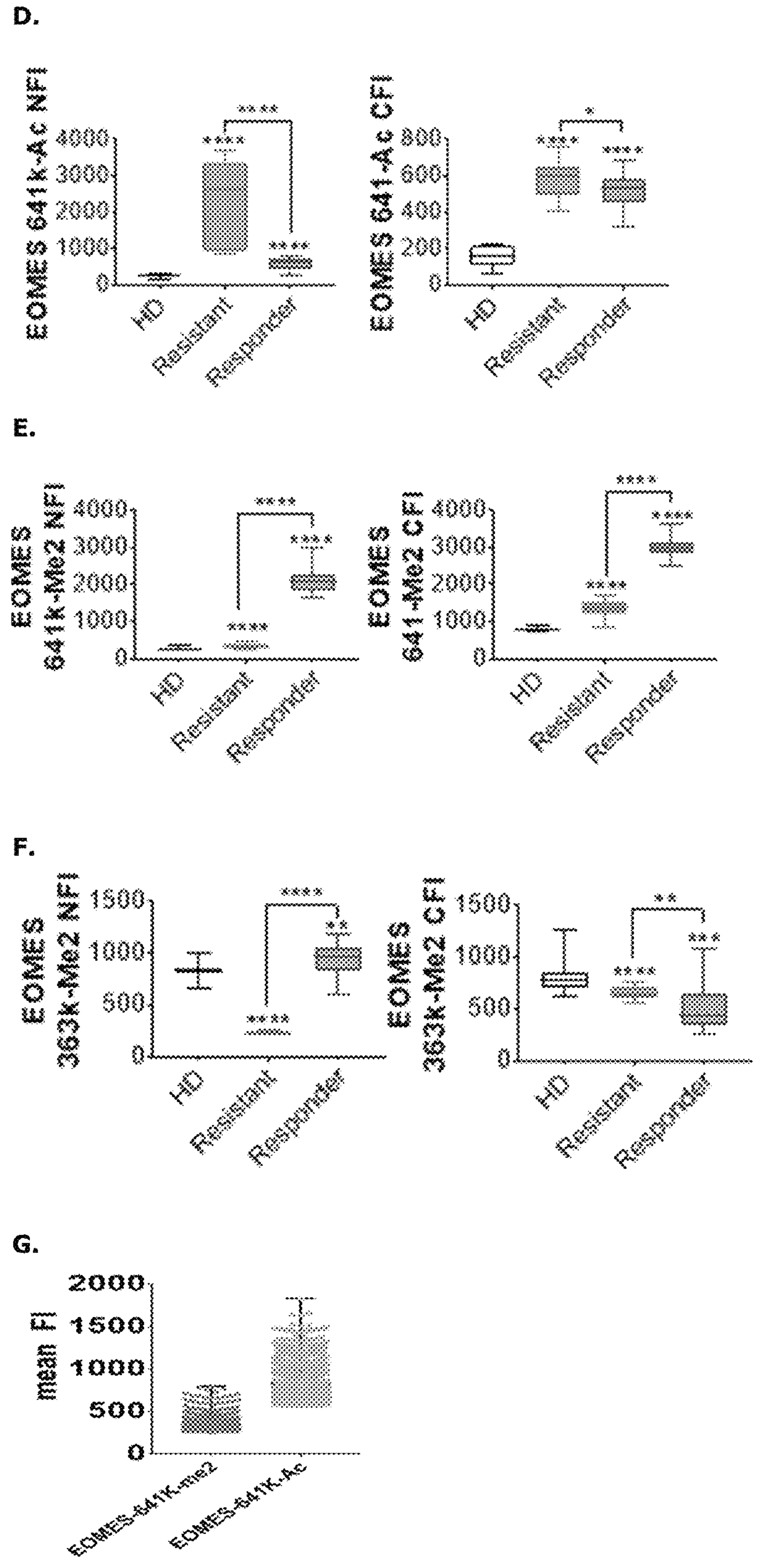

In addition to the identified EOMES NLS, a EOMES DNA-binding domain was also identified in the EOMES polypeptide at $^{364}$RQEISFGKLKLTNNKGANN$^{382}$, with a central lysine at position 373 (373K) critical for control of target binding specificity. A homology model of an EOMES: DNA complex was generated based on the X-ray structure of the DNA binding domain within the transcription factor T-bet, so as to assess the potential interaction regions between EOMES and DNA/chromatin/promoter regions. The high sequence identity between EOMES and T-BET (72%) within the DNA-binding domains provided a 100% confidence level in the model, with the overlay of EOMES and T-bet confirming the high similarity in these regions. The lysine at position 373 in EOMES is conserved in T-BET (373K), the latter of which was shown to associate with the phosphates on the DNA. Methylation of this lysine residue would be predicted to interfere with DNA binding (FIG. 3A). Rabbit polyclonal antibodies to EOMES containing methylation at this residue (i.e. EOMES-373K-Me) were also raised (FIGS. 2 and 3B).

The inventors hypothesized that the acetylation of EOMES-641K would be more prevalent in CD8$^+$ T-cell samples with higher exhaustion. It was also predicted that EOMES-641K-Me prevalence would be higher in more responsive CD8$^+$ T-cells along with EOMES-373K-Me. The profile of EOMES-641K-Me and EOMES-641K-Ac was therefore examined in baseline formalin-fixed paraffin-embedded (FFPE) tissue taken from two cohorts of melanoma patients; those either classified as responsive to immunotherapy or resistant to immunotherapy after treatment had commenced. Baseline FFPE tissue was taken before treatment had commenced. Analysis of protein expression via high resolution imaging revealed that EOMES-641K-Me is present in T-cells of both cohorts but at a significantly higher level in responder cohorts than resistant. The resistant cohort was the only cohort in which a significant intensity of EOMES-641K-Ac was observed, with the responder cohort having virtually no observable EOMES-641K-Ac (FIG. 3C; representative images not shown).

The relative presence of EOMES-641K-Me and EOMES-641K-Ac in baseline tissue may represent the base exhaustion signature of the patient sample, and whether it has the capacity to respond to immunotherapy alone. If there is a high prevalence of EOMES-641K-Ac, then it suggests that immunotherapy alone is not sufficient and additional therapeutic modality, such as an epigenetic drugs targeting EOMES-641K-Ac post-translational modification, may be needed.

EOMES-641K-Ac prevalence was then examined through high resolution microscopy of CD8$^+$ T-cells derived from either healthy donors, patients responsive to immunotherapy and patients resistant to immunotherapy. Analysis revealed that only CD8$^+$ T-cells from resistant, refractory patients had any significant levels of EOMES-641K-Ac, and this EOMES-641K-Ac was also predominately biased towards nuclear localization (FIG. 3D; representative images not shown).

EOMES-641K-Me was also profiled by high resolution microscopy of CD8$^+$ T-cells derived from healthy donors, patients responsive to immunotherapy or resistant to immunotherapy. Analysis revealed that CD8$^+$ T-cells from the responsive cohort had significantly higher levels of EOMES-641K-Me than T-cells from either the resistant, refractory patient cohort or the healthy donor cohort. EOMES-641K-Me was predominately biased towards cytoplasmic localization in all three cohorts, with significant nuclear expression of EOMES-641K-Me only being detected in CD8$^+$ T cells derived from responders (FIG. 3E; representative images not shown).

EOMES-373K-Me prevalence in CD8$^+$ T-cells from the same patient cohorts was also assessed by high resolution microscopy. Analysis revealed that CD8$^+$ T-cells from the responsive cohort had significantly higher levels of EOMES-373K-Me than the resistant, refractory patient cohort and, to a lesser extent, the healthy donor cohort. EOMES-373K-Me was also found to be predominately biased towards nuclear localization in responder cohorts only (FIG. 3F; representative images not shown).

Analysis of EOMES-641K-Me and EOMES-641K-Ac in CD8$^+$ T-cells derived from triple negative breast cancer (TNBC) patients revealed that these cells also have an EOMES signature that matches CD8$^+$ T-cells from resistant melanoma patients, suggesting that these T-cells from the TNBC patients are also exhausted (FIG. 3G; representative images not shown). Notably, TNBC does not respond well to immunotherapy.

In summary, EOMES-641K-Ac is associated with patients who are non-responders to immunotherapy, and can therefore can predict or classify patients as non-responders to immunotherapy. Conversely, EOMES-641K-Me and EOMES-373K-Me are associated with patients who are responders to immunotherapy, and can therefore predict or classify patients as responders to immunotherapy.

The data indicates that nuclear localization of EOMES is important for an exhaustive phenotype, keeping it in the acetylated form and demethylated at 641 and 373. For effector function, a state seen in healthy T-cells, EOMES is methylated and expressed in the cytoplasm, although is also present within the nucleus.

This data also suggests a novel role of EOMES. This factor can have positive and negative functions, based on specific post-translational modifications present at 641K and 373K. EOMES nuclear localization is also effect by the post-translational modifications at 641K, with EOMES-641K-Me been entirely cytoplasmic in CD8$^+$ T-cells from patients resistant to therapy, but localized also to the nucleus of cells from patients that respond to therapy.

Example 3

Figure 4:
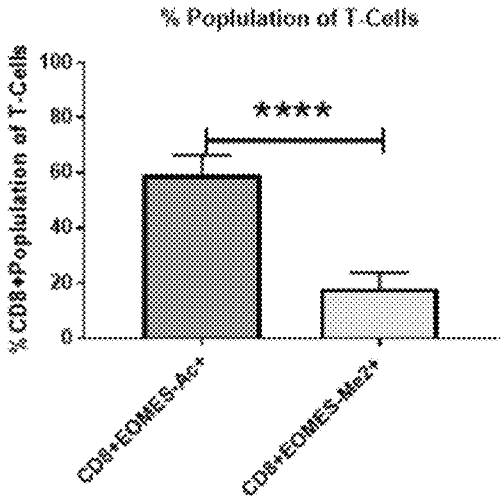
FIG. 4 is a graphical representation showing the prevalence of post-translationally modified EOMES in brain cancer metastatic lesions. Primary tumour brain FFPE sections from 10 patient samples were processed with using the BOND RX and OPAL-5 Colour automation kit from Perkin Elmer. FFPE tissues were fixed and immunofluorescence microscopy was performed using anti-EOMES-641K-Ac, anti-EOMES-641K-Me, anti-cytokeratin (a tumour marker) and anti-CD8 antibodies and DAPI staining (Green=EOMES-641K-Ac, Cyan=EOMES-EOMES-641K-Me, Red=CD8, Magenta=Cytokeratin, DAPI=blue) with Opal-kit dyes 520, 570, 650 and 690. The population % of $CD8^+$ T-cells positive for $CD8^+$ and EOMES-641K-Ac or EOMES-641K-Me was measured. (A) Graph plot represents the % population of $CD8^+$ T-cells positive for EOMES-641K-Ac or EOMES-641K-Me. (B) Graph plot represents the TFI (+/− standard error) for EOMES-641K-Ac and EOMES-641K-Me in $CD8^+$ T-Cells. (N at least 50000 cells profiled per a patient FFPE sample for N=10 patients).
Figure 4:
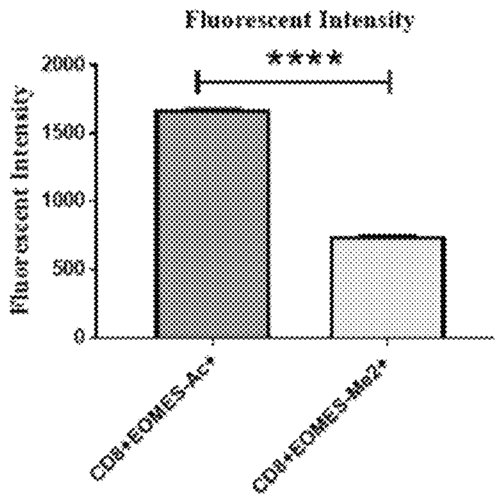

Eomes Localization in CD8$^+$ T-Cells from Patients with Metastatic Brain Cancer FFPE tissue from metastatic brain lesions from patients with metastatic brain cancer were examined via the automated ASI mIF system, targeting infiltrating CD8$^+$ T-cells expressing either EOMES-641K-Ac or EOMES-641K-Me. Interestingly, analysis found that CD8$^+$ T-cells within the tumour lesion that expressed EOMES-641K-Ac accounted for ~60% of the CD8$^+$ T-cell population whereas CD8$^+$ T-cells expressing EOMES-641K-Me accounted for just under 18% of the CD8$^+$ T-cell population. Additionally, intensity of expression for EOMES-641K-Ac was significantly higher than that of EOMES-641K-Me for CD8$^+$ T-cells within the lesion. This suggests that EOMES-641K-Ac is upregulated in CD8$^+$ T-cells within the cancer metastatic lesion in brain metastatic events, which is indicative of an exhausted CD8$^+$ T-cell signature. (FIG. 4; representative images not shown).

Example 4

Materials and Methods

Isolation of CD8$^+$ T-Cells

Metastatic melanoma biopsies were pre-enriched using the RosetteSep™ method to isolate CD8$^+$ T-cells. The RosetteSep™ Human CD8 enrichment kit (15063, Stemcell Technologies) was used to isolate CD8$^+$ T-Cells and remove red blood cells, using density gradient centrifugation with SepMate™-50 (IVD) density gradient tubes (85450, Stemcell Technologies) and Lymphoprep™ density gradient medium (07861, Stemcell Technologies).

Immunofluorescent Microscopy

Isolated CD8$^+$ T-cells or Jurkat cells were cytospun onto a coverslip pre-treated with poly-l-lysine and fixed then stored in PBS for staining. Cells were permeabilized by incubating with 1% Triton X-100 for 20 min and were probed with relevant antibodies including anti-CD8, anti TNF, anti-IFN-γ, anti-Ki67, anti-PD1, anti-EOMES, anti-TBET and anti-cytokeratin antibodies. Custom polyclonal rabbit anti-EOMES-641K-Ac, anti-EOMES-641K-Me and anti-EOMES-373K-Me were also used. Primary antibodies were visualized with a secondary antibody conjugated to Alexa Fluor 488 (anti-rabbit), 568 (anti-mouse) or 647 (anti-rat).

FFPE samples from metastatic lesion tumour biopsies were processed using BOND RX for OPAL staining (Perkin-Elmer) using the instrument protocol: ER2 for 20 mins at 100 °C with Epitope Retrieval Solution 1 (a pH6 EDTA based retrieval solution) followed by probing with rabbit anti-EOMES-641K-Ac or anti-EOMES-641K-Me, and mouse host CD8 and visualization with Opal Kit 520, 570 and 690.

Cover slips were mounted on glass microscope slides with ProLong Diamond Antifade reagent (Life Technologies). Protein targets were localized by confocal laser scanning microscopy. Single 0.5 μm sections were obtained using a Leica DMI8 microscope using 100× oil immersion lens running LAX software. The final image was obtained by averaging four sequential images of the same section. Digital images were analyzed using ImageJ software (ImageJ, NIH, Bethesda, MD, USA) to determine either the Total Fluorescent Intensity (TFI), Nuclear Fluorescent Intensity (NFI), the Cytoplasmic Fluorescent Intensity (CFI). The Mann-Whitney nonparametric test (GraphPad Prism, GraphPad Software, San Diego, CA) was used to determine significant . . . differences between datasets.

Generation of EOMES Antibodies

Antibodies were generated against the following peptides: EOMES NLS: VTSCKRRRLSP (SEQ ID NO:2); EOMES-641K-Ac: VTYSCK (Ac) RRRLSP (SEQ ID NO:3); EOMES-641K-Me: VTYSCK (Me) RRRLSP (SEQ ID NO:4); and EOMES-373K-Me: RQUISFGKLK (Me) LTNNKGANN (SEQ ID NO:5). As short peptides are generally not immunogenic in their own right, it is often necessary to couple them to immunogenic carrier proteins. To facilitate this coupling, a cysteine was incorporated at the C-terminus of the above peptide sequences and reacted to conjugate the peptide to an immunogenic carrier protein, Keyhole Limpet Hemocyanin (KLH). No special immunization protocols were required to generate anti-dimethylated or anti-acetylated peptide antibodies. Two or four rabbits for each peptide sequence were immunized several weeks apart. The first immunization was with an emulsion of the peptide conjugate with Complete Freund's adjuvant, the second using Incomplete Freund's adjuvant. Potent anti-peptide sera were obtained after several weeks (refer to Palfreyman, et al. (1984) *J Immunol Meth,* 75:383).

The testing of dimethylated and acetylated peptide antisera was performed using an enzyme linked immunosorbent assay (ELISA) where the sera were titrated on microtiter plates coated with non-postranslationally modified peptide, dimethylated peptide, or acetylated peptide.

Antibody enhancement was performed by coupling the unmodified peptide to a gel Sulfo Link Coupling Resin (Thermo Scientific, Catalogue number 20401) using the available cysteine residue, following the manufacturer's instructions. The resultant gel was incubated with aliquots of the antisera to absorb antibodies specific to the unmodified peptide. The resultant antiserum has an enhanced specificity for the dimethylated peptide or acetylated peptide sequences.

To produce affinity purified antibodies that are specific to the dimethylated or acetylated peptides only, the enhancement procedure was first performed to remove antibodies from the serum that are specific to the unmodified peptide. Specificity of the affinity purified antibodies was tested by ELISA. Generated antibodies showed high specificity for the various forms of peptides, as shown in FIG. 2.

ASI System Method (High Through Put, High Resolution Microscopy)

ASI's mIF system is a generic scan and analysis system for multiplexed immunofluorescent samples. It was designed to scan a slide stained with DAPI and up to 6 antibody stains, remove auto fluorescent, resolve unmixing between filters and perform cell-based analysis on the acquired data. Touching cells are automatically segmented, signal expression is quantitatively measured and results per cell and over entire scanned region are displayed. Various automated and semi-automated scanning modes are supported including:

1. Efficient Density-based scan for suspension samples-scanning the sample based on cell population for fastest cell scoring;
2. Scanning selective regions/areas; and
3. Interactive scanning of specific locations of interest.

In all modes, integrated statistics for thousands and tens of thousands of cells with co-localization of antibodies can be derived in minutes. 3D stacking, auto exposure, auto focus and other imaging parameters are inherent part of each scan. The images was used to determine the either the mean Nuclear Fluorescent Intensity (NFI) or overall Fluorescent Intensity (FI), Total number of cells were counted in a defined area using an automated stage and ASI software used to automatically select cells and measure fluorescent intensities. Resulting data was then employed to calculate CTC population dynamics expressed as a % of total cell population.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A method for treating a cancer patient with an immunotherapy, the method comprising:

(1) detecting in a sample taken from the patient a T-cell or population of T-cells that comprises a level of a post-translational modification in a nuclear localization sequence and/or a DNA binding motif of Eomesodermin (EOMES), wherein the post-translational modification is selected from the group consisting of EOMES-641K-Ac, EOMES-641K-Me and EOMES-373K-Me;

(2) stratifying the cancer patient as a likely responder to the immunotherapy if when a level of EOMES-641K-Me or EOMES-373K-Me is detected in the sample T-cell or population of T-cells at a higher level than a level of EOMES-641K-Me or EOMES-373K-Me in a dysfunctional exhausted T-cell or population of exhausted dysfunctional-T-cells, or as a likely non-responder to the immunotherapy if when a level of EOMES-641K-Ac is detected in the sample T-cell or population of T-cells at a higher level than a level of EOMES-641K-Ac in a functional T-cell or population of functional T-cells; and (3) administering the immunotherapy to the cancer patient stratified as a likely responder to the immunotherapy.

2. The method of claim 1, wherein the stratifying comprises detecting the level of EOMES-641K-Me in the T-cell or population of T-cells and stratifying the patient as a likely responder to the immunotherapy when the level of EOMES-641K-Me detected in the sample T-cell or population of T-cells is at a higher level than the level of EOMES-641K-Me in a exhausted T-cell or population of exhausted T-cells.

3. The method of claim 2, comprising contacting the sample with an antigen-binding molecule that binds specifically to EOMES-641K-Me, and detecting in the sample the level of a complex that comprises the antigen-binding molecule and the EOMES-641K-Me, and stratifying the patient as a likely responder to the immunotherapy when the level of the complex detected in the sample T-cell or population of T-cells is at a higher level than the level of the complex in a exhausted T-cell or population of exhausted T-cells.

4. The method of claim 1, wherein the stratifying comprises detecting the level of EOMES-373K-Me in the T-cell or population of T-cells and stratifying the patient as a likely responder to the immunotherapy when the level of EOMES-373K-Me detected in the sample T-cell or population of T-cells is at a higher level than the level of EOMES-373K-Me in a exhausted T-cell or population of exhausted T-cells.

5. The method of claim 4, comprising contacting the sample with an antigen-binding molecule that binds specifically to EOMES-373K-Me, and detecting in the sample the level of a complex that comprises the antigen-binding molecule and the EOMES-373K-Me, and stratifying the patient as a likely responder to the immunotherapy when the level of the complex detected in the sample T-cell or population of T-cells is at a higher level than the level of the complex in a exhausted T-cell or population of exhausted T-cells.

6. He method of claim 1, wherein the stratifying comprises detecting the level of EOMES-641K-Ac in the T-cell or T-cell population and stratifying the patient as a likely non-responder to the immunotherapy when the level of EOMES-641K-Ac detected in the sample T-cell or population of T-cells is at a higher level than the level of EOMES-641K-Ac in a functional T-cell or population of functional T-cells.

7. The method of claim 6, comprising contacting the sample with an antigen-binding molecule that binds specifically to EOMES-641K-Ac, and detecting in the sample the level of a complex that comprises the antigen-binding molecule and the EOMES-641K-Ac, and stratifying the patient as a likely non-responder to the immunotherapy when the level of the complex detected in the sample T-cell or population of T-cells is at a higher level than the level of the complex in a functional T-cell or population of functional T-cells.

8. The method of claim 1, comprising: contacting the sample with a first antigen-binding molecule that binds specifically to EOMES-641K-Ac and a second antigen-binding molecule that binds specifically to EOMES-641K-Me; measuring in the sample the level of a first complex that comprises the first antigen-binding molecule and EOMES-641K-Ac, and the level of a second complex that comprises the second antigen-binding molecule and EOMES-641K-Me, and comparing the level of the first complex to the level of the second complex; and stratifying the patient as a likely responder or non-responder based on the comparison, wherein the patient is stratified as a likely non-responder when the level of the first complex is higher than the second complex in the sample and wherein the patient is stratified as a likely responder when the level of the second complex is higher than the first complex.

9. The method of claim 1, further comprising detecting the level of at least one additional biomarker.

10. The method of claim 9, wherein the at least one additional biomarker is selected from the group consisting of IFN-γ, TNF-α, IL-2, Ki67, PD-1 and CD107a.

11. The method of claim 1, wherein the immunotherapy comprises therapy with an immune checkpoint inhibitor.

12. The method of claim 11, wherein the immune checkpoint inhibitor is an antagonist antibody or antigen-binding fragment thereof that binds specifically to an immune checkpoint molecule.

13. The method of claim 12, wherein the immune checkpoint molecule is PD-1, PD-L1 or CTLA4.

14. The method of claim 1, wherein the post-translational modification is detected in a $CD8^+$ T-cell or a population of $CD8^+$ T-cells.

* * * * *